US007214374B2

(12) United States Patent
Meyers et al.

(10) Patent No.: US 7,214,374 B2
(45) Date of Patent: May 8, 2007

(54) 12832, A NOVEL HUMAN KINASE-LIKE MOLECULE AND USES THEREOF

(75) Inventors: Rachel Meyers, Newton, MA (US); Martin R. Hodge, Arlington, MA (US); Mark Williamson, Saugus, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 211 days.

(21) Appl. No.: 10/682,739

(22) Filed: Oct. 9, 2003

(65) Prior Publication Data

US 2004/0147004 A1 Jul. 29, 2004

Related U.S. Application Data

(60) Division of application No. 09/562,480, filed on May 1, 2000, now Pat. No. 6,656,698, which is a continuation-in-part of application No. 09/345,473, filed on Jun. 30, 1999, now Pat. No. 6,558,903.

(51) Int. Cl.
*A61K 39/00* (2006.01)
*G01N 33/53* (2006.01)

(52) U.S. Cl. .................. 424/139.1; 435/7.1; 424/133.1; 424/134.1; 424/178.1

(58) Field of Classification Search ................ 530/300, 530/350; 435/6, 15, 194
See application file for complete search history.

(56) References Cited

U.S. PATENT DOCUMENTS 5,663,314 A * 9/1997 Seger et al. ................ 536/23.2

5,734,022 A * 3/1998 Pasternack ................ 530/387.1
5,817,479 A 10/1998 Au-Young et al.

FOREIGN PATENT DOCUMENTS

WO WO 99/64576 A2 12/1999
WO WO 00/06728 A2 2/2000

OTHER PUBLICATIONS

Brien et al., "Prognostic Factors in Gastric Cancer," Modern Pathology, vol. 11, No. 9, p. 870 (1998).*
Gorczyca et al., "Laser Scanning Cytometric Analysis of Cyclin B1 in Primary Human Malignancies," Modern Pathology, vol. 10, No. 5, p. 457 (1997).*
Suzuki et al., "T Cell-Dependent Antibody Responses against Aberrantly Expressed Cydin B1 Protein in Patients with Cancer and Premalignant Disease," Clinical Cancer Research, vol. 11, 1521-1526 (2005).*

(Continued)

*Primary Examiner*—Bruce R. Campell
*Assistant Examiner*—M. Franco Salvoza

(57) ABSTRACT

Novel human kinase-like polypeptides, proteins, and nucleic acid molecules are disclosed. In addition to isolated, full-length kinase-like proteins, the invention further provides isolated kinase-like fusion proteins, antigenic peptides, and anti-kinase-like antibodies. The invention also provides kinase-like nucleic acid molecules, recombinant expression vectors containing a nucleic acid molecule of the invention, host cells into which the expression vectors have been introduced, and nonhuman transgenic animals in which a kinase-like gene has been introduced or disrupted. Diagnostic, screening, and therapeutic methods utilizing compositions of the invention are also provided.

14 Claims, 8 Drawing Sheets

OTHER PUBLICATIONS

NCBI Entrez Protein Query, GenBank Report for Accession No. AAB71795, Federspiel et al., Direct Submission, Submitted Jun. 5, 1997. Amino Acid Residues 1-645 are SEQ Nos. 15 and 16.

NCBI Entrez Protein Query, GenBank Report for Accession No. AAB65490, Rounsley et al., Direct Submission, Submitted Apr. 4, 1997. Amino Acid Residues 1-604 are SEQ No. 17.

NCBI Entrez Protein Query, GenBank Report for Accession No. AAC47047, Wilson et al., "2-2 Mb of Contiguous Nucleotide Sequence from Chromosome III of C. elegans," Nature, 1994, pp. 32-38, vol. 368: Waterson, Direct Submission, Submitted Apr. 8, 1994. Amino Acid Residues 1-328 are SEQ No. 18.

NCBI Entrez Protein Query, GenBank Report for Accession No. P80192, Dorow et al., "Identification of a New Family of Human Epithelial Protein Kinase Containing Two Leucine/Isoleucine-zipper Domains," Eur. J. Biochem., 1993, pp. 701-710, vol. 213. Amino Acid Residues 1-394 are SEQ No. 19.

NCBI Entrez Protein Query, GenBank Report for Accession No. AAB70848, Loomis et al., Direct Submission, Submitted Aug. 20, 1997. Amino Acid Residues 1 to 256 are SEQ No. 20.

NCBI Entrez Protein Query, GenBank Report for Accession No. AAB51171, Lamerdin, Direct Submission, Submitted Nov. 8, 1996. Amino Acid Residues 1 to 1237 are SEQ No. 21.

NCBI Entrez Protein Query, GenBank Report for Accession No. BAA25487, O'Hara et al., Direct Submission, Submitted Feb. 13, 1998. Amino Acid Residues 1 to 1308 are SEQ No. 22.

NCBI Entrez Protein Query, GenBank Report for Accession No. BAA34527, Nagase et al., "Prediction of the Coding Sequences of Unidentified Human Genes. XI. The Complete Sequences of 100 new cDNA Clones from Brain which Code for Large Proteins in Vitro," DNA Res., 1998, pp. 277-286, vol. 5: O'Hara et al., Direct Submission, Submitted Oct. 8, 1998. Amino Acid Residues 1 to 1265 are SEQ No. 23.

NCBI Entrez Protein Query, GenBank Report for Accession No. AAC04312, Walden et al., "A Novel 205-kDa Testis-specific Serine/Threonine Protein Kinase Associated with Microtubules of the Spermatid Manchette," Mol. Cell Biol, pp. 7625-7635, vol. 13: Walden, Direct Submission, Submitted Oct. 4, 1993. Amino Acid Residues 1 to 1734 are SEQ No. 24.

NCBI Entrez Protein Query, GenBank Report for Accession No. P38938, Samejima et al., "Identification of Cut8+ and cek1+, a Novel Protein Kinase Gene, which Complement a Fission Yeast Mutation that Blocks Anaphase," Mol. Cell Biol., 1994, pp. 6361-6371, vol. 14: Amino Acid Residues 1 to 1309 are SEQ No. 25.

NCBI Entrez Protein Query, GenBank Report for Accession No. P23049, Smith et al., "The V-Sea Oncogene of Avian Erythroblastosis Retrovirus S13: Another Member of the Protein-tyrosine Kinase Gene Family," Proc. Natl. Acad. Sci. USA, 1989, pp. 5291-5295, vol. 86: Amino Acids Residues 1 to 370 are SEQ No. 26.

NCBI Entrez Protein Query, GenBank Report for Accession No. TVFSA, Smith et al., "The V-Sea Oncogene of Avian Erythroblastosis Retrovirus S13: Another Member of the Protein-tyrosine Kinase Gene Family," Proc. Natl. Acad. Sci. USA, 1989, pp. 5291-5295, vol. 86: Amino Acid Residues 1 to 596 are SEQ No. 27.

NCBI Entrez Protein Query, GenBank Report for Accession No. AAC19211, Wilson et al., "2-2 Mb of Contiguous Nucleotide Sequence from Chromosome III of C. elegans," Nature, 1994, pp. 32-38, vol. 368: Amino Acid Residues 1 to 430 are SEQ No. 28.

NCBI Entrez Protein Query, GenBank Report for Accession No. P18475, Sprenger et al., "The Drosophila Gene Torso Encodes a Putative Receptor Tyrosine Kinase," Nature, 1989, pp. 478-483, vol. 338, Amino Acid Residues 1 to 923 are SEQ No. 29.

NCBI Entrez Protein Query, GenBank Report for Accession No. AAA48729, Huff et al., "The Protooncogene C-Sea Encodes a Transmembrane Protein-tyrosine Kinase Related to the Met/Hepatocyte Growth Factor/Scatter Factor Receptor," Proc. Natl. Acad. Sci. USA, 1993, pp. 6140-6144, vol. 90: Amino Acid Residues 1 to 1404 are SEQ No. 30.

NCBI Entrez Protein Query, GenBank Report for Accession No. AAA65223, Chen et al., Direct Submission, Submitted Apr. 4, 1995. Amino Acid Residues 1-891 are SEQ No. 31.

NCBI Entrez Protein Query, GenBank Report for Accession No. AAC47258, McCoon et al., SpFGFR, A New Member of the Fibroblast Growth Factor Receptor Family, Is Developmentally Regulated during Early Sea Urchin Development, J. Biol. Chem, 1996, pp. 20119-20125, vol. 371: Amino Acid Residues 1 TO 972 are SEQ No. 32.

NCBI Entrez Protein Query, GenBank Report for Accession No. AAd30583, Federspiel et al., Direct Submission, Submitted Apr. 8, 1999, Amino Acid Residues 1 to 355 are SEQ No. 33.

NCBI Entrez Protein Query, GenBank Report for Accession No. CAB43919, Bevan et al., Direct Submission, Submitted May 31, 1999. Amino Acid Residues 1 to 669 are SEQ No. 34.

NCBI Entrez Protein Query, GenBank Report for Accession No. AAC24561, Waterston, Direct Submission, Submitted Jan. 15, 1998. Amino Acid Residues 1 to 540 are SEQ No. 35.

NCBI Entrez Protein Query, GenBank Report for Accession No. Q13546, Hsu et al., "TNF-dependent Recruitment of the Protein Kinase RIP to TNF Receptor-1 Signaling Complex," Immunity, 1996, pp. 387-394, vol. 4: Amino Acid Residues 1 to 671 are SEQ No. 36.

NCBI Entrez Protein Query, GenBank Report for Accession No. Q60855, Stanger et al., "RIP" A Novel Protein Containing a Death Domain that Interacts with Fas/APO-1 (CD95) in Yeast and Causes Cell Death, Cell 1995, pp. 513-523, vol. 81: Amino Acid Residues 1 to 656 are SEQ No. 37.

NCBI Entrez Protein Query, GenBank Report for Accession No. AAD02059, Chen et al., Direct Submission, Submitted Dec. 3, 1997. Amino Acid Residues 1 to 142 are SEQ No. 38.

NCBI Entrez Protein Query, GenBank Report for Accession No. CAB43520, Cooke et al., Direct Submission, Submitted May 14, 1999. Amino Acid Residues 1 to 36 are SEQ No. 39.

NCBI Entrez Protein Query, GenBank Report for Accession No. AAC18797, Theologis, Direct Submission, Submitted Dec. 9, 1997. Amino Acid Residues 1 to 525 are SEQ No. 40.

NCBI Entrez Protein Query, GenBank Report for Accession No. CAB41172, Choisne et al., Direct Submission, Submitted Jun. 9, 1999. Amino Acid Residues 1 to 502 are SEQ No. 41.

NCBI Entrez Protein Query, GenBank Report for Accession No. CAA99887, Wilson et al., "2-2 Mb of Contiguous Nucleotide Sequence from Chromosome III of C. elegans," Nature, 1994, pp. 32-38, vol. 368: McMurray, Direct Submission, Submitted Jun. 29, 1996. Amino Acid Residues 1 to 461 are SEQ No. 42.

NCBI Entrez Protein Query, GenBank Report for Accession No. CAA15621, Wilson et al., "2-2 Mb of Contiguous Nucleotide Sequence from Chromosome III of C. elegans," Nature, 1994, pp. 32-38, vol. 368: McMurray, Direct Submission, Submitted Nov. 14, 1997. Amino Acid Residues 1 to 231 are SEQ No. 42.

NCBI Entrez Protein Query, GenBank Report for Accession No. CAB44308, Jordan, Direct Submission, Submitted May 28, 1999. Amino Acid Residues 1 to 309 are SEQ No. 44.

NCBI Entrez Protein Query, GenBank Report for Accession No. AAC32599, Kim et al., Direct Submission, Submitted Jul. 27, 1999. Amino Acid Residues 1 to 647 are SEQ No. 45.

NCBI Entrez Protein Query, GenBank Report for Accession No. Q01577, Ruiz-Perez, "PkpA, A Novel *Physomyces blakesleeanus* Serine/Threonine Protein Kinase," Curr. Genet, 1995, pp. 309-316, vol. 28: Amino Acid Residues 1 to 571 are SEQ No. 46.

NCBI Entrez Protein Query, GenBank Report for Accession No. CAA92591, Wilson et al., "2-2 Mb of Contiguous Nucleotide Sequence from Chromosome III of C. elegans," Nature, 1994, pp. 32-38, vol. 368: McMurray, Direct Submission, Submitted Dec. 20, 1995. Amino Acid Residues 251 to 1851 are SEQ No. 47.

NCBI Entrez Protein Query, GenBank Report for Accession No. P53671, Okano et al., "Identification and Characterization of a Novel Family of Serine/Threonine Kinases Containing Two N-Terminal LIM Motifs," J. Biol. Chem., 1995, pp. 31321-31330, vol. 270: Amino Acid Residues 1 to 638 are SEQ No. 48.

NCBI Entrez Protein Query, GenBank Report for Accession No. AAB54055, Waterston, Direct Submission, Submitted May 12, 1997. Amino Acid Residues 1 to 733 are SEQ No. 49.

NCBI Entrez Protein Query, GenBank Report for Accession No. Q15569, Toshima et al., "Identification and Characterization of a Novel Protein Kinase, TESK1, Specifically Expressed in Testicular Germ Cells," *J. Biol. Chem.*, 1995, pp. 31331-31337, vol. 270: Amino Acid Residues 1 to 626 are SEQ No. 50.

NCBI Entrez Protein Query, GenBank Report for Accession No. BAA24489, Mizuno, Direct Submission, Submitted Jun. 24, 1997. Amino Acid Residues 1 to 617 are SEQ No. 51.

NCBI Entrez Protein Query, GenBank Report for Accession No. BAA31147, Mizuno et al., Direct Submission, Submitted Mar. 9, 1998. Amino Acid Residues 1 to 451 are SEQ No. 52.

NCBI Entrez Protein Query, GenBank Report for Accession No. BAA25124, Toshima, Direct Submission, Submitted May 1, 1997. Amino Acid Residues 1 to 627 are SEQ No. 53.

NCBI Entrez Protein Query, GenBank Report for Accession No. BAA25125, Toshima, Direct Submission, Submitted May 1, 1997. Amino Acid Residues 1 to 627 are SEQ No. 54.

NCBI Entrez Protein Query, GenBank Report for Accession No. Q63572, Toshima et al., "Identification and Characterization of a Novel Protein Kinase, TESK1, Specifically Expressed in Testicular Germ Cells," *J. Biol. Chem.*, 1995, pp. 31331-31337, vol. 270: Amino Acid Residues 1 to 628 are SEQ No. 55.

NCBI Entrez Protein Query, GenBank Report for Accession No. BAA21488, Takahashi et al., Direct Submission, Submitted Feb 27, 1997. Amino Acid Residues 1 to 615 are SEQ No. 56.

NCBI Entrez Protein Query, GenBank Report for Accession No. AAC69038, Wilson et al., "2-2 Mb Of Contiguous Nucleotide Sequence from Chromosome III of *C. elegans*," *Nature*, 1994, pp. 32-38, vol. 368: Amino Acid Residues 1 to 653 are SEQ No. 57.

NCBI Entrez Protein Query, GenBank Report for Accession No. AAC24522, Eichinger et al., "Characterization and Cloning of a Dictyostelium ste20-line Protein Kinase that Phosphorylates the Actin-binding Protein Severin," *J. Biol. Chem.*, 1998, pp. 12952-12959, vol. 273: Amino Acid Residues 1 to 478 are SEQ No. 58.

NCBI Entrez Protein Query, GenBank Report for Accession No. CAA67700, Pombo et al., "Activation of a Human Ste20-like Kinase by Oxidant Stress Defines a Novel Stress Response Pathway," *EMBO J.*, 1996, pp. 4537-4546, vol. 15: Amino Acid Residues 1 to 426 are SEQ No. 59.

NCBI Entrez Protein Query, GenBank Report for Accession No. AAB82560, Schinkmann et al., "Cloning and Characterization of a Novel Mammalian Ste20-like Kinase (mst-3)," *J. Biol. Chem.*, 1997, In Press. 9, Amino Acid Residues 1 to 431 are SEQ No. 60.

NCBI Entrez Protein Query, GenBank Report for Accession No. BAA20420, Osada, Direct Submission, Submitted Jul. 3, 1995. Amino Acid Residues 1 to 426 are SEQ No. 61.

NCBI Entrez Protein Query, GenBank Report for Accession No. AAD01208, Melnick, Direct Submission, Submitted May 20, 1997. Amino Acid Residues 1 to 426 are SEQ No. 62.

Blast N Analysis of SEQ ID No. 1 vs. Nucleotide Patent Database.

Blast X Analysis of SEQ ID No. 2 vs PNU Database.

Blast X Analysis of SEQ ID No. 2 vs. Protein Patent Database.

Blast N ORF (open reading frame) Analysis of SEQ ID No. 1 vs. Nucleotide dbEST, Nucleotide Patent Review, and Nucleotide Patent Databases; and Blast X Analysis of SEQ ID No. 2 vs Protein and Protein Patent Databases.

Blast N Analysis of SEQ ID No. 3 vs. Nucleotide Patent and Nucleotide Patent Preview Databases.

Blast X Analysis of SEQ ID No. 4 vs. PNU and Protein Patent Databases.

Blast N Analysis of ORF of SEQ ID No. 3 vs. Nucleotide, dbEST, Nucleotide Patent Review, and Nucleotide Patent Databases; and Blast X Analysis of SEQ ID No. 4 vs Protein and Protein Patent Databases.

Blast N Analysis of SEQ ID No. 5 vs. Nucleotide, dbEST, Nucleotide Patent Review, and Nucleotide Patent Databases; and Blast X Analysis of SEQ ID No. 6 vs. Protein and Protein Patent Databases.

Blast N Analysis of ORF of SEQ ID No. 7 vs. Nucleotide, dbEST, Nucleotide Patent Review, and Nucleotide Patent Databases; and Blast X Analysis of SEQ ID No. 8 vs Protein and Protein Patent Databases.

Blast N Analysis of ORF of SEQ ID No. 9 vs. Nucleotide, dbEST, Nucleotide Patent Review, and Nucleotide Patent Databases; and Blast X Analysis of SEQ ID No. 10 vs Protein and Protein Patent Databases.

Blast N Analysis of ORF of SEQ ID No. 11 vs. Nucleotide, dbEST, Nucleotide Patent Review, and Nucleotide Patent Databases; and Blast X Analysis of SEQ ID No. 12 vs Protein and Protein Patent Databases.

Blast N Analysis of ORF of SEQ ID No. 13 vs. Nucleotide, dbEST, Nucleotide Patent Review, and Nucleotide Patent Databases; and Blast X Analysis of SEQ ID No. 14 vs Protein and Protein Patent Databases.

Database EST, Accession No. AA740847, NCI-CGAP http://www.Ncbi.nlm.nih.gov/ncicgap, 'National Cancer Institute, Cancer Genome Project (CGAP), Tumor Gene Index,' Feb. 7, 1998.

Database EST, Accession No. AA448898, Hillier et al., 'WashU-Merck EST Project,' Jun. 4, 1997.

Blast N Analysis of SEQ ID No. 1 vs. Nucleotide Patent Database, Sep. 19, 1999.

Blast X Analysis of SEQ ID No. 2 vs PNU Database, Sep. 29, 1999.

Blast X Analysis of SEQ ID No. 2 vs. Protein Patent Database, Sep. 29, 1999.

Blast N ORF (open reading frame) Analysis of SEQ ID No. 1 vs. Nucleotide dbEST, Nucleotide Patent Review, and Nucleotide Patent Databases; and Blast X Analysis of SEQ ID No. 2 vs Protein and Protein Patent Databases, Sep. 29, 1999.

* cited by examiner

Input file h12832; Output File h12832.pat
Sequence length 1586

```
GTCGACCCACGCGTCCGGTTCGAATTGCAACGGCAGCTGCCGGGCGTATGTGTTGGTGCTAGAGGCAGCTGCAGGGTCT    79
CGCTGGGGGCCGCTCGGGACCAATTTTGAAGAGGTACTTGGCCACGACTTATTTTCACCTCCGACCTTTCCTTCCAGGC   158
```

|   |   |   |   |   |   |   |   |   | M | E | G | I | S | N | F | K | T | P | S | 11 |
|---|---|---|---|---|---|---|---|---|---|---|---|---|---|---|---|---|---|---|---|---|
| GGTGAGACTCTGGACTGAGAGTGGCTTTCACA | | | | | | | | | ATG | GAA | GGG | ATC | AGT | AAT | TTC | AAG | ACA | CCA | AGC | 223 |

| K | L | S | E | K | K | K | S | V | L | C | S | T | P | T | I | N | I | P | A | 31 |
|---|---|---|---|---|---|---|---|---|---|---|---|---|---|---|---|---|---|---|---|---|
| AAA | TTA | TCA | GAA | AAA | AAG | AAA | TCT | GTA | TTA | TGT | TCA | ACT | CCA | ACT | ATA | AAT | ATC | CCG | GCC | 283 |

| S | P | F | M | Q | K | L | G | F | G | T | G | V | N | V | Y | L | M | K | R | 51 |
|---|---|---|---|---|---|---|---|---|---|---|---|---|---|---|---|---|---|---|---|---|
| TCT | CCG | TTT | ATG | CAG | AAG | CTT | GGC | TTT | GGT | ACT | GGG | GTA | AAT | GTG | TAC | CTA | ATG | AAA | AGA | 343 |

| S | P | R | G | L | S | H | S | P | W | A | V | K | K | I | N | P | I | C | N | 71 |
|---|---|---|---|---|---|---|---|---|---|---|---|---|---|---|---|---|---|---|---|---|
| TCT | CCA | AGA | GGT | TTG | TCT | CAT | TCT | CCT | TGG | GCT | GTA | AAA | AAG | ATT | AAT | CCT | ATA | TGT | AAT | 403 |

| D | H | Y | R | S | V | Y | Q | K | R | L | M | D | E | A | K | I | L | K | S | 91 |
|---|---|---|---|---|---|---|---|---|---|---|---|---|---|---|---|---|---|---|---|---|
| GAT | CAT | TAT | CGA | AGT | GTG | TAT | CAA | AAG | AGA | CTA | ATG | GAT | GAA | GCT | AAG | ATT | TTG | AAA | AGC | 463 |

| L | H | H | P | N | I | V | G | Y | R | A | F | T | E | A | N | D | G | S | L | 111 |
|---|---|---|---|---|---|---|---|---|---|---|---|---|---|---|---|---|---|---|---|---|
| CTT | CAT | CAT | CCA | AAC | ATT | GTT | GGT | TAT | CGT | GCT | TTT | ACT | GAA | GCC | AAT | GAT | GGC | AGT | CTG | 523 |

| C | L | A | M | E | Y | G | G | E | K | S | L | N | D | L | I | E | E | R | Y | 131 |
|---|---|---|---|---|---|---|---|---|---|---|---|---|---|---|---|---|---|---|---|---|
| TGT | CTT | GCT | ATG | GAA | TAT | GGA | GGT | GAA | AAG | TCT | CTA | AAT | GAC | TTA | ATA | GAA | GAA | CGA | TAT | 583 |

| K | A | S | Q | D | P | F | P | A | A | I | I | L | K | V | A | L | N | M | A | 151 |
|---|---|---|---|---|---|---|---|---|---|---|---|---|---|---|---|---|---|---|---|---|
| AAA | GCC | AGC | CAA | GAT | CCT | TTT | CCA | GCA | GCC | ATA | ATT | TTA | AAA | GTT | GCT | TTG | AAT | ATG | GCA | 643 |

| R | G | L | K | Y | L | H | Q | E | K | K | L | L | H | G | D | I | K | S | S | 171 |
|---|---|---|---|---|---|---|---|---|---|---|---|---|---|---|---|---|---|---|---|---|
| AGA | GGG | TTA | AAG | TAT | CTG | CAC | CAA | GAA | AAG | AAA | CTG | CTT | CAT | GGA | GAC | ATA | AAG | TCT | TCA | 703 |

| N | V | V | I | K | G | D | F | E | T | I | K | I | C | D | V | G | V | S | L | 191 |
|---|---|---|---|---|---|---|---|---|---|---|---|---|---|---|---|---|---|---|---|---|
| AAT | GTT | GTA | ATT | AAA | GGC | GAT | TTT | GAA | ACA | ATT | AAA | ATC | TGT | GAT | GTA | GGA | GTC | TCT | CTA | 763 |

| P | L | D | E | N | M | T | V | T | D | P | E | A | C | Y | I | G | T | E | P | 211 |
|---|---|---|---|---|---|---|---|---|---|---|---|---|---|---|---|---|---|---|---|---|
| CCA | CTG | GAT | GAA | AAT | ATG | ACT | GTG | ACT | GAC | CCT | GAG | GCT | TGT | TAC | ATT | GGC | ACA | GAG | CCA | 823 |

| W | K | P | K | E | A | V | E | E | N | G | V | I | T | D | K | A | D | I | F | 231 |
|---|---|---|---|---|---|---|---|---|---|---|---|---|---|---|---|---|---|---|---|---|
| TGG | AAA | CCC | AAA | GAA | GCT | GTG | GAG | GAG | AAT | GGT | GTTT | ATT | ACT | GAC | AAG | GCA | GAC | ATA | TTT | 883 |

| A | F | G | L | T | L | W | E | M | M | T | L | S | I | P | H | I | N | L | S | 251 |
|---|---|---|---|---|---|---|---|---|---|---|---|---|---|---|---|---|---|---|---|---|
| GCC | TTT | GGC | CTT | ACT | TTG | TGG | GAA | ATG | ATG | ACT | TTA | TCG | ATT | CCA | CAC | ATT | AAT | CTT | TCA | 943 |

| N | D | D | D | D | E | D | K | T | F | D | E | S | D | F | D | D | E | A | Y | 271 |
|---|---|---|---|---|---|---|---|---|---|---|---|---|---|---|---|---|---|---|---|---|
| GCC | TTT | GGC | CTT | ACT | TTG | TGG | GAA | ATG | ATG | ACT | TTA | TCG | ATT | CCA | CAC | ATT | AAT | CTT | TCA | 1003 |

| Y | A | A | L | G | T | R | P | P | I | N | M | E | E | L | D | E | S | Y | Q | 291 |
|---|---|---|---|---|---|---|---|---|---|---|---|---|---|---|---|---|---|---|---|---|
| TAT | GCA | GCG | TTG | GGA | ACT | AGG | CCA | CCT | ATT | AAT | ATG | GAA | GAA | CTG | GAT | GAA | TCA | TAC | CAG | 1063 |

| K | V | I | E | L | F | S | V | C | T | N | E | D | P | K | D | R | P | S | A | 311 |
|---|---|---|---|---|---|---|---|---|---|---|---|---|---|---|---|---|---|---|---|---|
| AAA | GTA | ATT | GAA | CTC | TTC | TCT | GTA | TGC | ACT | AAT | GAA | GAC | CCT | AAA | GAT | CGT | CCT | TCT | GCT | 1123 |

| A | H | I | V | E | A | L | E | T | D | V | * |   |   |   |   |   |   |   |   | 322 |
|---|---|---|---|---|---|---|---|---|---|---|---|---|---|---|---|---|---|---|---|---|
| GCA | CAC | ATT | GTT | GAA | GCT | CTG | GAA | ACA | GAT | GTC | TAG | | | | | | | | | 1159 |

```
TGATCATCTCAGCTGAAGTGTGGCTTGCGTAAATAACTGTTTATTCCAAAATATTTACATAGTTACTATCAGTAGTTAT 1238
TAGACTCTAAAATTGGCATATTTGAGGACCATAGTTTCTTGTTAACATATGGATAACTATTTCTAATATGAAATATGCT 1317
```

FIG. 1A.

TATATTGGCTATAAGCACTTGGAATTGTACTGGGTTTTCTGTAAAGTTTTAGAAACTAGCTACATAAGTACTTTGATAC 1396
TGCTCATGCTGACTTAAAACACTAGCAGTAAAACGCTGTAAACTGTAACATTAAATTGAATGACCATTACTTTTATTAA 1475
TGATCTTTCTTAAATATTCTATATTTTAATGGATCTACTGACATTAGCACTTTGTACAGTACAAAATAAAGTCTACATT 1554
TGTTTAAAAAAAAAAAAAAAAAAGGGCGGCCGC 1586

FIG. 1B.

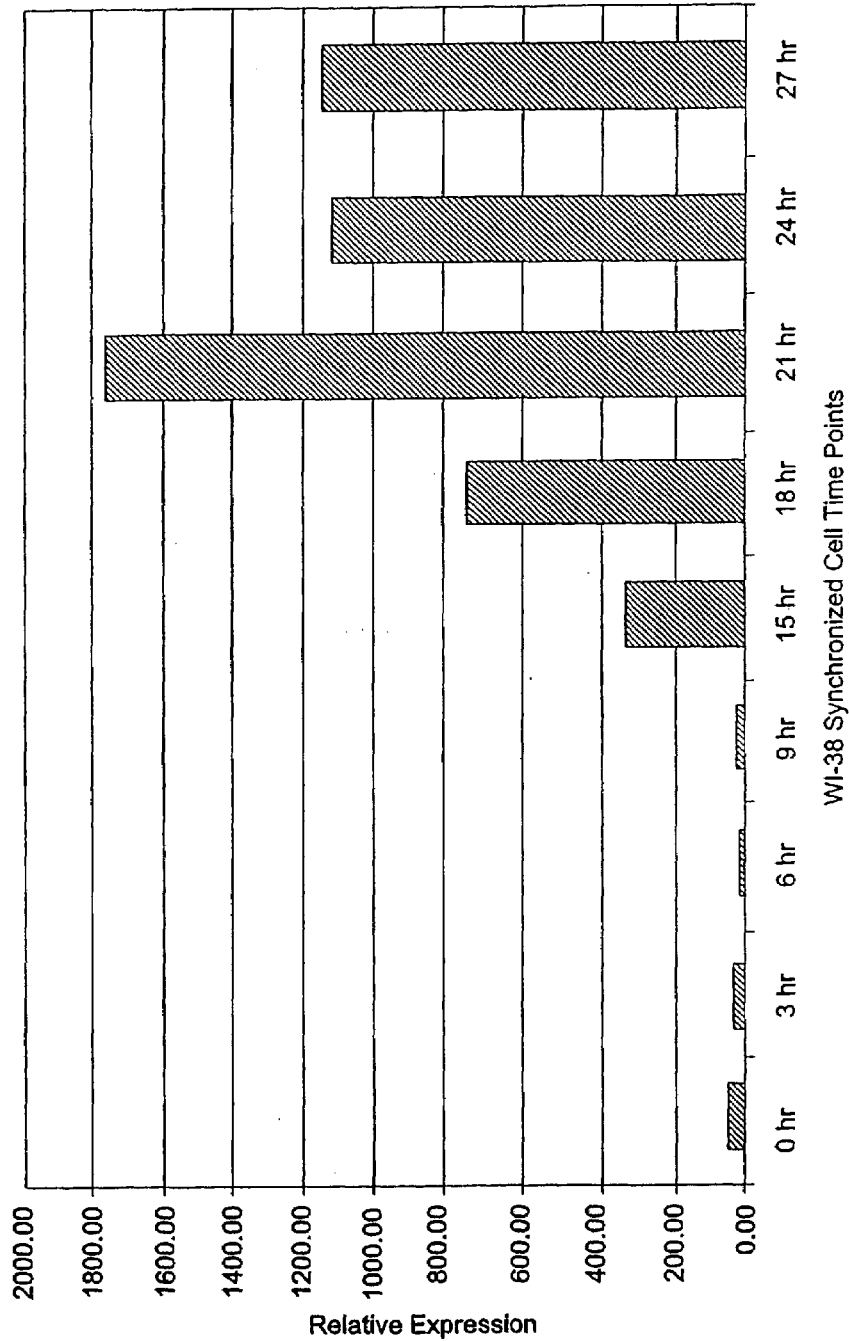

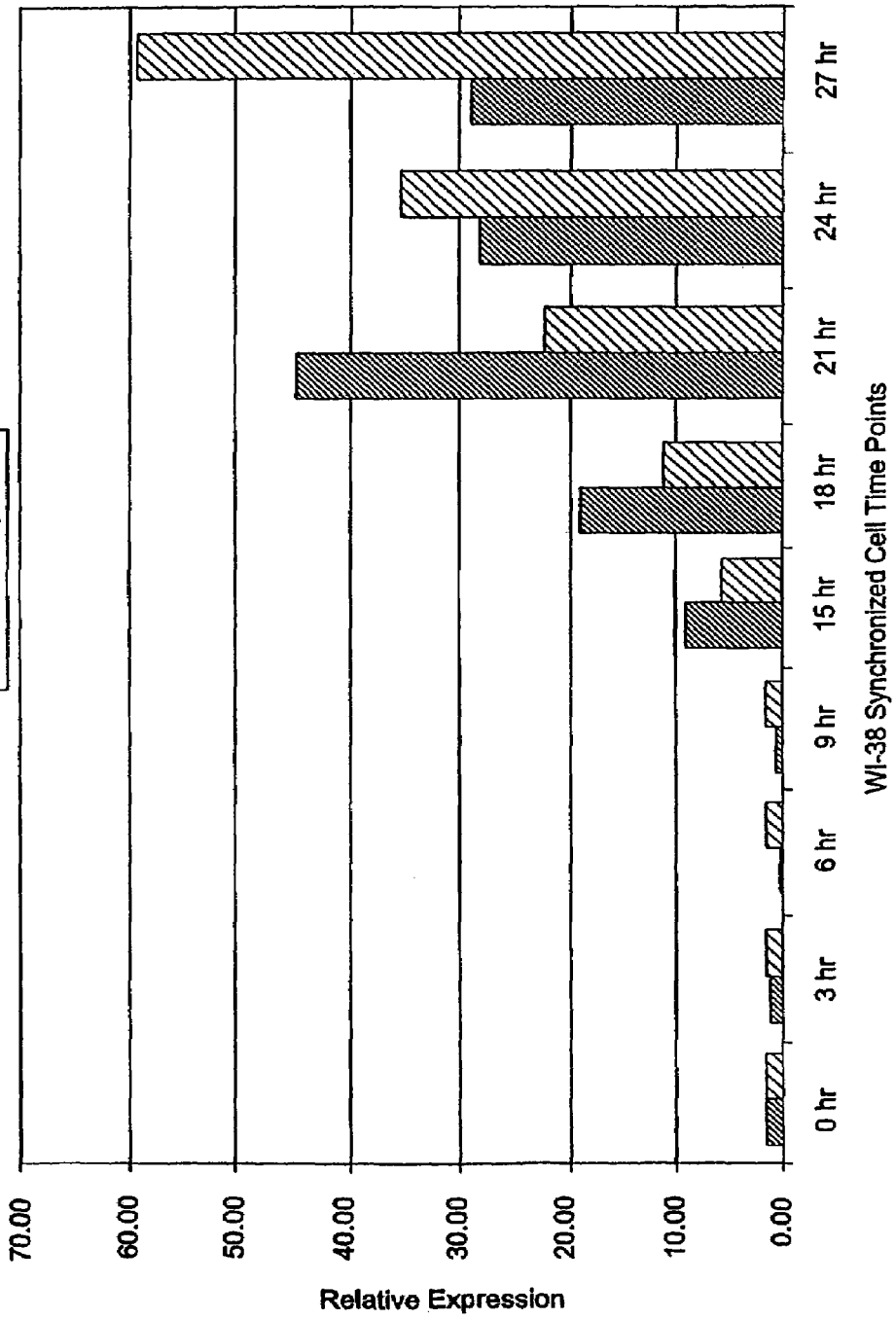

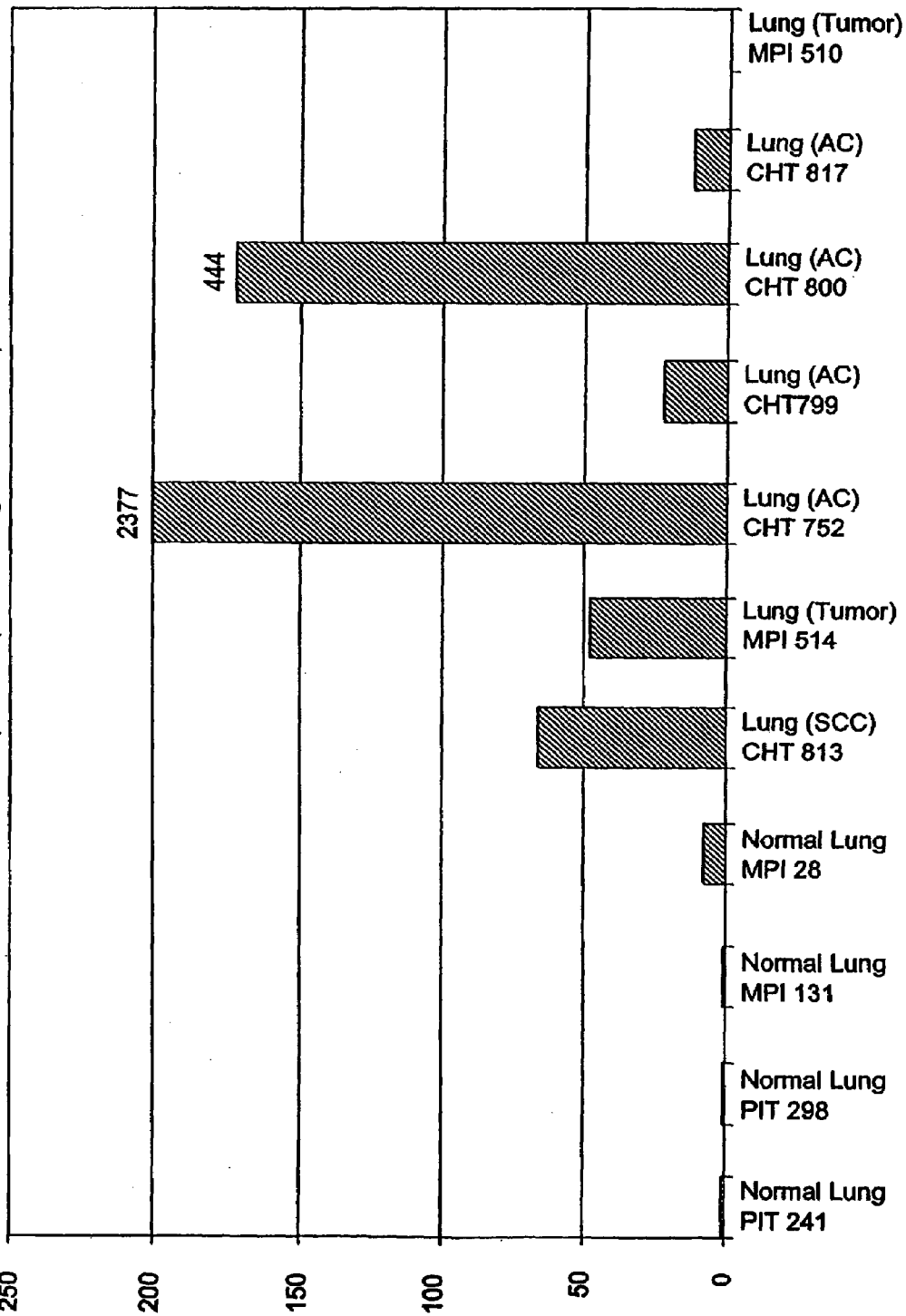

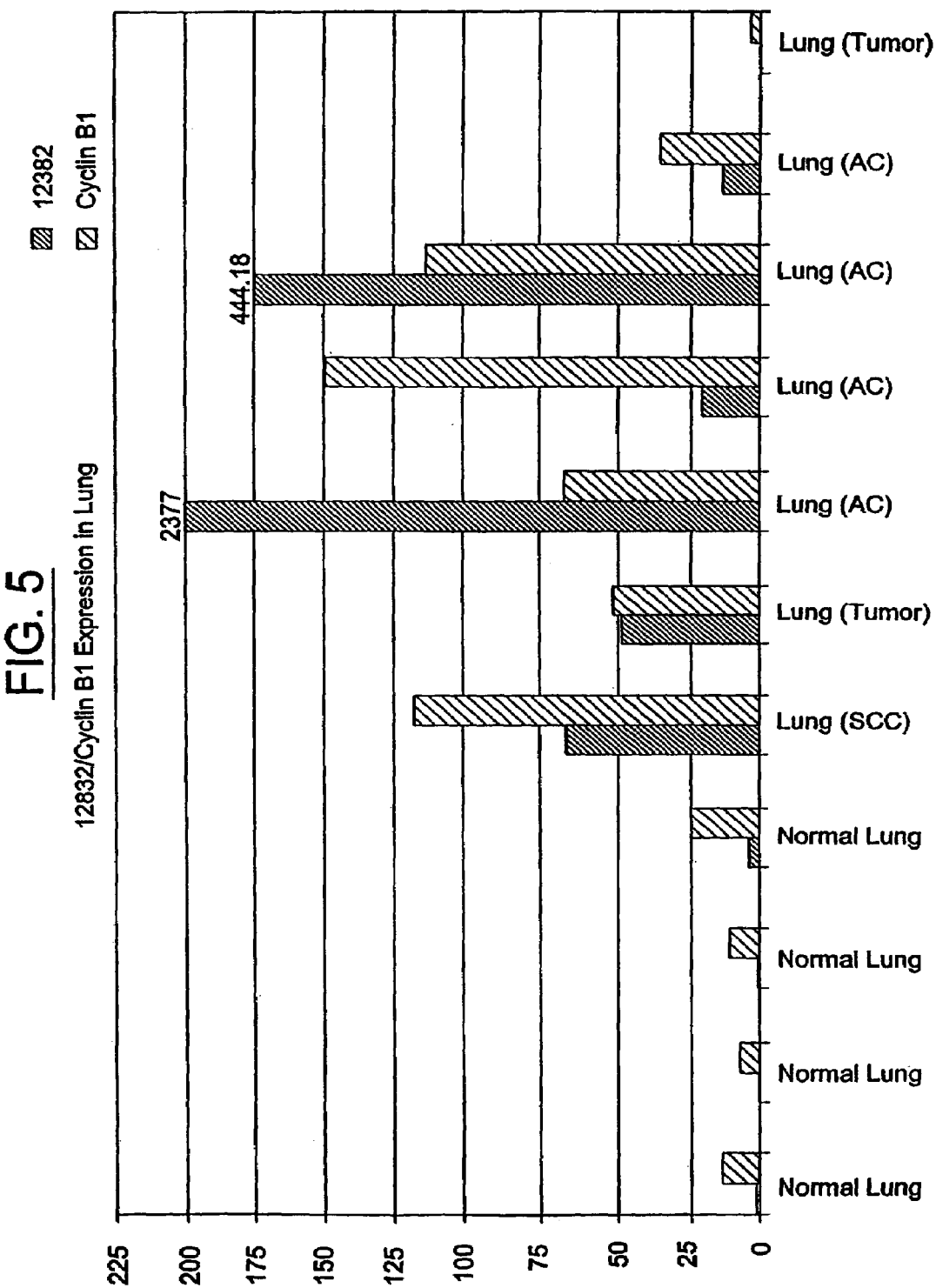

SEQUENCE LISTING

```
<160> NUMBER OF SEQ ID NOS: 2

<210> SEQ ID NO 1
<211> LENGTH: 1586
<212> TYPE: DNA
<213> ORGANISM: Homo sapiens
<220> FEATURE:
<221> NAME/KEY: CDS
<222> LOCATION: (191)...(1156)

<400> SEQUENCE: 1
gtcgacccac gcgtccggtt cgaattgcaa cggcagctgc cgggcgtatg tgttggtgct      60
agaggcagct gcagggtctc gctgggggcc gctcgggacc aattttgaag aggtacttgg     120
ccacgactta ttttcacctc cgacctttcc ttccaggcgg tgagactctg gactgagagt     180
ggctttcaca atg gaa ggg atc agt aat ttc aag aca cca agc aaa tta        229
            Met Glu Gly Ile Ser Asn Phe Lys Thr Pro Ser Lys Leu
              1               5                  10 tca gaa aaa aag aaa tct gta tta tgt tca act cca act ata aat atc       277
Ser Glu Lys Lys Lys Ser Val Leu Cys Ser Thr Pro Thr Ile Asn Ile
 15                  20                  25 ccg gcc tct ccg ttt atg cag aag ctt ggc ttt ggt act ggg gta aat       325
Pro Ala Ser Pro Phe Met Gln Lys Leu Gly Phe Gly Thr Gly Val Asn
 30                  35                  40                  45 gtg tac cta atg aaa aga tct cca aga ggt ttg tct cat tct cct tgg       373
Val Tyr Leu Met Lys Arg Ser Pro Arg Gly Leu Ser His Ser Pro Trp
                 50                  55                  60 gct gta aaa aag att aat cct ata tgt aat gat cat tat cga agt gtg       421
Ala Val Lys Lys Ile Asn Pro Ile Cys Asn Asp His Tyr Arg Ser Val
             65                  70                  75 tat caa aag aga cta atg gat gaa gct aag att ttg aaa agc ctt cat       469
Tyr Gln Lys Arg Leu Met Asp Glu Ala Lys Ile Leu Lys Ser Leu His
         80                  85                  90 cat cca aac att gtt ggt tat cgt gct ttt act gaa gcc aat gat ggc       517
His Pro Asn Ile Val Gly Tyr Arg Ala Phe Thr Glu Ala Asn Asp Gly
     95                 100                 105
```

```
agt ctg tgt ctt gct atg gaa tat gga ggt gaa aag tct cta aat gac      565
Ser Leu Cys Leu Ala Met Glu Tyr Gly Gly Glu Lys Ser Leu Asn Asp
110                 115                 120                 125 tta ata gaa gaa cga tat aaa gcc agc caa gat cct ttt cca gca gcc      613
Leu Ile Glu Glu Arg Tyr Lys Ala Ser Gln Asp Pro Phe Pro Ala Ala
            130                 135                 140 ata att tta aaa gtt gct ttg aat atg gca aga ggg tta aag tat ctg      661
Ile Ile Leu Lys Val Ala Leu Asn Met Ala Arg Gly Leu Lys Tyr Leu
        145                 150                 155 cac caa gaa aag aaa ctg ctt cat gga gac ata aag tct tca aat gtt      709
His Gln Glu Lys Lys Leu Leu His Gly Asp Ile Lys Ser Ser Asn Val
    160                 165                 170 gta att aaa ggc gat ttt gaa aca att aaa atc tgt gat gta gga gtc      757
Val Ile Lys Gly Asp Phe Glu Thr Ile Lys Ile Cys Asp Val Gly Val
175                 180                 185 tct cta cca ctg gat gaa aat atg act gtg act gac cct gag gct tgt      805
Ser Leu Pro Leu Asp Glu Asn Met Thr Val Thr Asp Pro Glu Ala Cys
190                 195                 200                 205 tac att ggc aca gag cca tgg aaa ccc aaa gaa gct gtg gag gag aat      853
Tyr Ile Gly Thr Glu Pro Trp Lys Pro Lys Glu Ala Val Glu Glu Asn
            210                 215                 220 ggt gtt att act gac aag gca gac ata ttt gcc ttt ggc ctt act ttg      901
Gly Val Ile Thr Asp Lys Ala Asp Ile Phe Ala Phe Gly Leu Thr Leu
        225                 230                 235 tgg gaa atg atg act tta tcg att cca cac att aat ctt tca aat gat      949
Trp Glu Met Met Thr Leu Ser Ile Pro His Ile Asn Leu Ser Asn Asp
    240                 245                 250 gat gat gat gaa gat aaa act ttt gat gaa agt gat ttt gat gat gaa      997
Asp Asp Asp Glu Asp Lys Thr Phe Asp Glu Ser Asp Phe Asp Asp Glu
255                 260                 265 gca tat tat gca gcg ttg gga act agg cca cct att aat atg gaa gaa     1045
Ala Tyr Tyr Ala Ala Leu Gly Thr Arg Pro Pro Ile Asn Met Glu Glu
270                 275                 280                 285 ctg gat gaa tca tac cag aaa gta att gaa ctc ttc tct gta tgc act     1093
Leu Asp Glu Ser Tyr Gln Lys Val Ile Glu Leu Phe Ser Val Cys Thr
            290                 295                 300 aat gaa gac cct aaa gat cgt cct tct gct gca cac att gtt gaa gct     1141
Asn Glu Asp Pro Lys Asp Arg Pro Ser Ala Ala His Ile Val Glu Ala
        305                 310                 315 ctg gaa aca gat gtc tagtgatcat ctcagctgaa gtgtggcttg cgtaaataac     1196
Leu Glu Thr Asp Val
            320 tgtttattcc aaaatattta catagttact atcagtagtt attagactct aaaattggca   1256 tatttgagga ccatagtttc ttgttaacat atggataact atttctaata tgaaatatgc   1316 ttatattggc tataagcact tggaattgta ctgggttttc tgtaaagttt tagaaactag   1376 ctacataagt actttgatac tgctcatgct gacttaaaac actagcagta aaacgctgta   1436 aactgtaaca ttaaattgaa tgaccattac ttttattaat gatctttctt aaatattcta   1496 tattttaatg gatctactga cattagcact ttgtacagta caaaataaag tctacatttg   1556 tttaaaaaaa aaaaaaaaaa gggcggccgc                                    1586

<210> SEQ ID NO 2
<211> LENGTH: 322
<212> TYPE: PRT
<213> ORGANISM: Homo sapiens

<400> SEQUENCE: 2
```

-continued

```
Met Glu Gly Ile Ser Asn Phe Lys Thr Pro Ser Lys Leu Ser Glu Lys
 1               5                  10                  15
Lys Lys Ser Val Leu Cys Ser Thr Pro Thr Ile Asn Ile Pro Ala Ser
             20                  25                  30
Pro Phe Met Gln Lys Leu Gly Phe Gly Thr Gly Val Asn Val Tyr Leu
         35                  40                  45
Met Lys Arg Ser Pro Arg Gly Leu Ser His Ser Pro Trp Ala Val Lys
     50                  55                  60
Lys Ile Asn Pro Ile Cys Asn Asp His Tyr Arg Ser Val Tyr Gln Lys
 65                  70                  75                  80
Arg Leu Met Asp Glu Ala Lys Ile Leu Lys Ser Leu His His Pro Asn
             85                  90                  95
Ile Val Gly Tyr Arg Ala Phe Thr Glu Ala Asn Asp Gly Ser Leu Cys
            100                 105                 110
Leu Ala Met Glu Tyr Gly Gly Glu Lys Ser Leu Asn Asp Leu Ile Glu
            115                 120                 125
Glu Arg Tyr Lys Ala Ser Gln Asp Pro Phe Pro Ala Ala Ile Ile Leu
        130                 135                 140
Lys Val Ala Leu Asn Met Ala Arg Gly Leu Lys Tyr Leu His Gln Glu
145                 150                 155                 160
Lys Lys Leu Leu His Gly Asp Ile Lys Ser Ser Asn Val Val Ile Lys
                165                 170                 175
Gly Asp Phe Glu Thr Ile Lys Ile Cys Asp Val Gly Val Ser Leu Pro
            180                 185                 190
Leu Asp Glu Asn Met Thr Val Thr Asp Pro Glu Ala Cys Tyr Ile Gly
        195                 200                 205
Thr Glu Pro Trp Lys Pro Lys Glu Ala Val Glu Glu Asn Gly Val Ile
    210                 215                 220
Thr Asp Lys Ala Asp Ile Phe Ala Phe Gly Leu Thr Leu Trp Glu Met
225                 230                 235                 240
Met Thr Leu Ser Ile Pro His Ile Asn Leu Ser Asn Asp Asp Asp Asp
                245                 250                 255
Glu Asp Lys Thr Phe Asp Glu Ser Asp Phe Asp Asp Glu Ala Tyr Tyr
        260                 265                 270
Ala Ala Leu Gly Thr Arg Pro Pro Ile Asn Met Glu Glu Leu Asp Glu
        275                 280                 285
Ser Tyr Gln Lys Val Ile Glu Leu Phe Ser Val Cys Thr Asn Glu Asp
    290                 295                 300
Pro Lys Asp Arg Pro Ser Ala Ala His Ile Val Glu Ala Leu Glu Thr
305                 310                 315                 320
Asp Val
```

US 7,214,374 B2

12832, A NOVEL HUMAN KINASE-LIKE MOLECULE AND USES THEREOF

CROSS-REFERENCE TO RELATED APPLICATION

This application is a divisional application of U.S. application Ser. No. 09/562,480, filed May 1, 2000, now U.S. Pat. No. 6,656,698; which is a continuation-in-part of U.S. patent application Ser. No. 09/345,473 filed Jun. 30, 1999, now U.S. Pat. No. 6,558,903, each of which is hereby incorporated in its entirety by reference.

FIELD OF THE INVENTION

The invention relates to novel human kinase-like nucleic acid sequences and proteins. Also provided are vectors, host cells, and recombinant methods for making and using the novel molecules.

BACKGROUND OF THE INVENTION

Phosphate tightly associated with a molecule, e.g., a protein, has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated molecules, e.g., proteins, implies the existence of one or more kinases, e.g., protein kinases, capable of phosphorylating various molecules, e.g., amino acid residues on proteins, and also of phosphatases, e.g., protein phosphatases, capable of hydrolyzing various phosphorylated molecules, e.g., phosphorylated amino acid residues on proteins.

Protein kinases play critical roles in the regulation of biochemical and morphological changes associated with cellular growth and division (D'Urso et al. (1990) *Science* 250:786–791; Birchmeier et al. (1993) *Bioessays* 15:185–189). They serve as growth factor receptors and signal transducers and have been implicated in cellular transformation and malignancy (Hunter et al. (1992) *Cell* 70:375–387; Posada et al. (1992) *Mol. Biol. Cell* 3:583–592; Hunter et al. (1994) *Cell* 79:573–582). For example, protein kinases have been shown to participate in the transmission of signals from growth-factor receptors (Sturgill et al. (1988) *Nature* 344:715–718; Gomez et al. (1991) *Nature* 353: 170–173), control of entry of cells into mitosis (Nurse (1990) *Nature* 344:503–508; Maller (1991) *Curr. Opin. Cell Biol.* 3:269–275) and regulation of actin bundling (Husain-Chishti et al. (1988) *Nature* 334:718–721).

Protein kinases can be divided into different groups based on either amino acid sequence similarity or specificity for either serine/threonine or tyrosine residues. A small number of dual-specificity kinases have also been described. Within the broad classification, kinases can be further subdivided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks et al. (1988) *Science* 241:42–52).

The entry and progression of cells through the cell cycle are controlled by changes in the levels and activities of cyclins. The levels of several of the cyclins (A, B, and E) peak during specific phases of the cell cycle, then are rapidly degraded as the cell enters the next phase of the cell cycle. Cyclins perform their function by forming complexes with a group of constitutively expressed proteins called cyclin-depended kinases (CDKs). Different combinations of cyclins and CDKs are associated with each of the important transitions in the cell cycle.

Cyclin B is synthesized and binds to CDK1 during the transition of the cell into the G2 phase of the cell cycle. This forms the B/CDK1 complex which is necessary for the cells to enter the M phase. The complex is activated by phosphorylation, and the active kinase then phosphorylates a variety of proteins involved in mitosis, DNA replication, depolymerization of the nuclear lamina, and mitotic spindle formation.

Kinases play a role in the transduction of signals for cell proliferation, differentiation, and apoptosis. Alteration in such genes and their products are frequent in human cancers. Deregulated cell proliferation is the hallmark of cancer. Alteration in such genes and their products are frequent in human cancer. Modulation of these genes and their regulatory activities may permit the control of tumor cell proliferation and invasion.

Kinases play critical roles in cellular growth. Therefore, novel kinase polynucleotides and proteins are useful for modulating cellular growth, differentiation and/or development.

SUMMARY OF THE INVENTION

Isolated nucleic acid molecules corresponding to kinase-like nucleic acid sequences are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:2 or the nucleotide sequences encoding the DNA sequence deposited in a bacterial host as ATCC Accession Number PTA-2342. Further provided are kinase-like polypeptides having an amino acid sequence encoded by a nucleic acid molecule described herein.

The present invention also provides vectors and host cells for recombinant expression of the nucleic acid molecules described herein, as well as methods of making such vectors and host cells and for using them for production of the polypeptides or peptides of the invention by recombinant techniques.

The kinase-like molecules of the present invention are useful for modulating cell growth, cell transformation, cellular signal transduction, and apoptosis. The molecules are useful for the diagnosis and treatment of any disorder wherein there is aberrant cell growth and/or division or aberrant signal transduction. Alterations in such molecules are frequent in human cancer. A cell cycle-regulated kinase designated clone 12832 is disclosed. Modulation of 12832 and kinase-like molecules of the invention may permit control of tumor cell proliferation and invasion. More specifically, these molecules are useful for the diagnosis and treatment of cellular growth, cellular cycling, and cellular differentiation involving the following human tissues: heart, lung, skin, testis, colon, thymus, tonsil, lymph node, placenta, fetal heart, fetal liver, fetal spinal cord, and undifferentiated and differentiated osteoblasts. Accordingly, in one aspect, this invention provides isolated nucleic acid molecules encoding kinase-like proteins or biologically active portions thereof, as well as nucleic acid fragments suitable as primers or hybridization probes for the detection of kinase-like-encoding nucleic acids.

Another aspect of this invention features isolated or recombinant kinase-like proteins and polypeptides. Preferred kinase-like proteins and polypeptides possess at least one biological activity possessed by naturally occurring kinase-like proteins.

Variant nucleic acid molecules and polypeptides substantially homologous to the nucleotide and amino acid sequences set forth in the sequence listings are encompassed by the present invention. Additionally, fragments and substantially homologous fragments of the nucleotide and amino acid sequences are provided.

Antibodies and antibody fragments that selectively bind the kinase-like polypeptides and fragments are provided. Such antibodies are useful in detecting the kinase-like polypeptides. In another aspect, the present invention provides a method for detecting the presence of kinase-like activity or expression in a biological sample by contacting the biological sample with an agent capable of detecting an indicator of kinase-like activity such that the presence of kinase-like activity is detected in the biological sample.

In yet another aspect, the invention provides a method for modulating kinase-like activity comprising contacting a cell with an agent that modulates (inhibits or stimulates) kinase-like activity or expression such that kinase-like activity or expression in the cell is modulated. In one embodiment, the agent is an antibody that specifically binds to kinase-like protein. In another embodiment, the agent modulates expression of kinase-like protein by modulating transcription of a kinase-like gene, splicing of a kinase-like mRNA, or translation of a kinase-like mRNA. In yet another embodiment, the agent is a nucleic acid molecule having a nucleotide sequence that is antisense to the coding strand of the kinase-like mRNA or the kinase-like gene.

In one embodiment, the methods of the present invention are used to treat a subject having a disorder characterized by aberrant kinase-like protein activity or nucleic acid expression by administering an agent that is a kinase-like modulator to the subject. In one embodiment, the kinase-like modulator is a kinase-like protein. In another embodiment, the kinase-like modulator is a kinase-like nucleic acid molecule. In other embodiments, the kinase-like modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding a kinase-like protein; (2) misregulation of a gene encoding a kinase-like protein; and (3) aberrant post-translational modification of a kinase-like protein, wherein a wild-type form of the gene encodes a protein with a kinase-like activity.

In another aspect, the invention provides a method for identifying a compound that binds to or modulates the activity of a kinase-like protein. In general, such methods entail measuring a biological activity of a kinase-like protein in the presence and absence of a test compound and identifying those compounds that alter the activity of the kinase-like protein.

The invention also features methods for identifying a compound that modulates the expression of kinase-like genes by measuring the expression of the kinase-like sequences in the presence and absence of the compound.

Other features and advantages of the invention will be apparent from the following detailed description and claims.

BRIEF DESCRIPTION OF THE DRAWINGS

FIGS. 1A and 1B provide the nucleotide and amino acid sequence (SEQ ID NO: 1 and 2, respectively) for clone 12832.

FIG. 2 shows 12832 expression in synchronized WI-38 cells. WI-38 cells (human lung fibroblasts) were synchronized by serum starvation. RNA was harvested in 3 hour intervals for 24 hours to capture cells in various cell cycle phases. First strand cDNA was synthesized and Taqman was done using 12832 primers on time points 0, 3, 6, 9, 15, 18, 21, 24 and 27 hours. FIG. 2 shows the expression level of 12832 during each phase of the WI-38 cell cycle.

FIG. 3 shows 12832 expression versus cyclin B 1 expression in synchronized WI-38 cells. Cyclin B1 is a marker for cell proliferation. The significant co-expression of cyclin B1 with 12832 supports the role of 12832 in tumor cell proliferation.

FIG. 4 shows 12832 expression in normal human lung tissue and in lung tumors. Taqman was done across a panel of human lung normal tissue and lung tumors. This Figure shows that 12832 expression is upregulated in 6/7 lung tumors verus normal lung tissue. The Y axis is relative expression. The X axis samples are as follows: PIT 241 normal lung, PIT 298 normal lung, MPI 131 normal lung, MPI 28 normal lung, CHT 813 lung (SSC), MPI 514 m lung (tumor), CHT 752 lung (AC), CHT 799 lung (AC), CHT 800 lung (AC), CHT 817 lung (AC), MPI 150 lung (tumor). The numbers 2377 and 444 represent the true expression values of these two samples. (AC represents adenocarcinoma; SSC represents squamous cell carcinoma).

FIG. 5 shows 12832 expression versus cyclin B1 expression in lung. Taqman across a panel of normal lung tissue and lung tumors shows 12832 expression correlates with cyclin B1 expression, indicating a potential role in lung tumor cell proliferation. (AC represents adenocarcinoma; SCC represents squamous cell carcinoma).

DETAILED DESCRIPTION OF THE INVENTION

Figure 6:
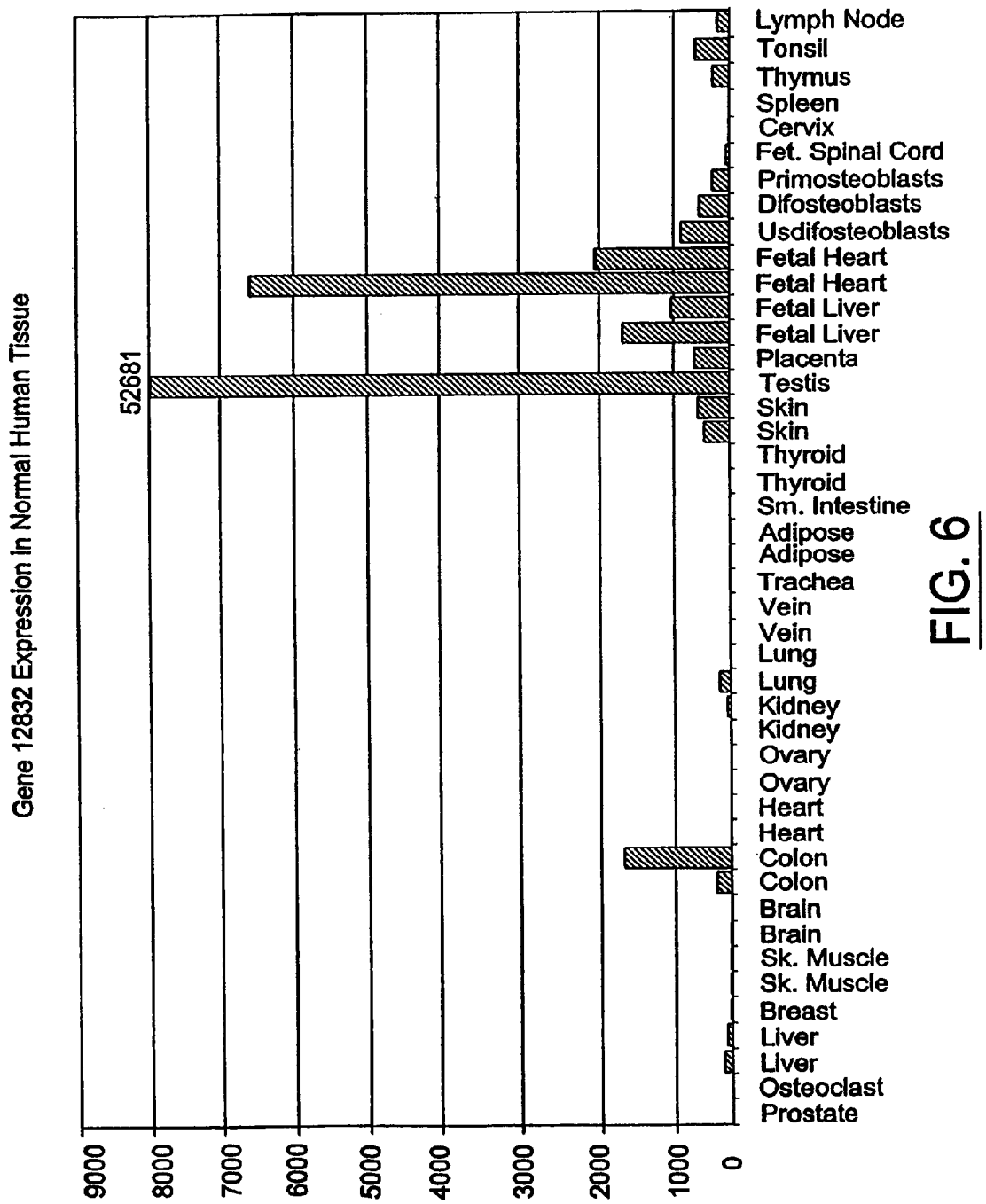
FIG. 6 shows 12832 gene expression in normal human tissues. Taqman across a panel of normal human tissue shows 12832 expression in proliferative normal tissues such as the testis and fetal liver and heart. (Y axis represents relative expression values).

The present invention provides kinase-like molecules. By "kinase-like molecules" is intended a novel human sequence referred to as 12832, and variants and fragments thereof. These full-length gene sequences or fragments thereof are referred to as "kinase-like" sequences, indicating they share sequence similarity with kinase genes. Isolated nucleic acid molecules comprising nucleotide sequences encoding the 12832 polypeptide whose amino acid sequence is given in SEQ ID NO:2, or a variant or fragment thereof, are provided. A nucleotide sequence encoding the 12832 polypeptide is set forth in SEQ ID NO:1. The sequences are members of the family of protein kinases. Protein kinases can be divided into different groups based on either amino acid sequence similarity or specificity for either serine/threonine or tyrosine residues. A small number of dual specificity kinases have been described.

As used herein the term "kinase" includes a protein, polypeptide, or other nonproteinaceous molecule that is capable of modulating its own phosphorylation state or the phosphorylation state of a different protein, polypeptide, or other nonproteinaceous molecule. Kinases can have specificity for (i.e., a specificity to phosphorylate) serine/threonine residues, tyrosine residues, or both serine/threonine and tyrosine residues, e.g., the dual-specificity kinases. As referred to herein, kinases such as protein kinases preferably include a catalytic domain of about 200–400 amino acid residues in length, or more preferably about 250–300 amino acid residues in length, which includes preferably 5–20, more preferably 5–15, or most preferably 11 highly conserved motifs or subdomains separated by sequences of amino acids with minimal conservation. Specificity of a kinase for phosphorylation of either tyrosine or serine/threonine can be predicted by the sequence of two subdomains (VIb and VIII) in which different residues are conserved in each class (as described in, for example, Hanks et al., (1988) Science 241: 42–52, the contents of which are incorporated herein by reference). These subdomains are also described in further detail herein.

A novel huma kinase-like gene sequence referred to as 12832 is provided. This gene sequence and variants and fragments thereof are encompassed by the term "kinase-like" molecules or sequences as used herein. The kinase-like sequences find use in modulating a kinase-like function. By "modulating" is intended the upregulating or downregulating of a response. That is, the compositions of the invention affect the targeted activity in either a positive or negative fashion.

The disclosed invention relates to methods and compositions for the modulation, diagnosis, and treatment of disorders related to aberrant cellular signal transduction, cell growth, cell cycling and division, including but not limited to various malignancies and cancers. The invention relates to all signaling pathways associated with cellular growth. For example, protein kinases are involved in the regulation of signal transmission from cellular receptors, e.g., growth-factor receptors, entry of cells into mitosis, and the regulation of cytoskeleton function, e.g., actin bundling.

Inhibition or over-stimulation of the activity of kinases involved in signaling pathways associated with cellular growth can lead to perturbed cellular growth, which can in turn lead to cellular growth-related disorders. As used herein, a "cellular growth-related disorder" includes a disorder, disease, or condition characterized by a deregulation, e.g., an upregulation or downregulation of cellular growth. Cellular growth deregulation may be due to a deregulation of cellular proliferation, cell cycle progression, cellular differentiation and/or cellular hypertrophy. Examples of cellular growth related disorders include but are not limited to cardiovascular disorders such as heart failure, hypertension, atrial fibrillation, dilated cardiomyopathy, or angina; proliferative disorders or differentiative disorders such as cancer., e.g., melanoma, prostrate cancer, cervical cancer, breast cancer, colon cancer, or sarcoma. Disorders associated with the following cells or tissues are also encompassed: lymph node, tonsil, thymus, liver, breast, skeletal muscle, colon, lung, skin, testis, placenta, small intestine, fetal liver, fetal heart, fetal spinal chord, undifferentiated and differentiated osteoblasts.

Clone 12832 encodes a 1.6 kb mRNA transcript having the corresponding cDNA set forth in SEQ ID NO:1. This transcript encodes a 322 amino acid protein (SEQ ID NO:2). The molecule may have transmembrane segments from amino acids (aa) 19–35 and 230–250 as predicted by MEM-SAT. Prosite program analysis was used to predict various sites within the 12832 protein. N-glycosylation sites were predicted at aa 196–199, and 249–252. Protein kinase C phosphorylation sites were predicted at aa 14–16, 52–54, 181–183, and 225–227. Casein kinase II phosphorylation sites were predicted at aa 122–125, 198–201, 236–239, 251–254, 260–263, 264–267, and 301–304. N-myristoylation sites were predicted at aa 41–46 and 118–123. A serine/threonine protein kinase active-site signature was predicted at aa 163–175. The 12832 protein possesses a eukaryotic protein kinase domain, from aa 32 to aa 316, as predicted by HHMer, Version 2. Within this domain, critical residues are conserved at amino acid (aa) positions 39, 41, 46, 62, 64 85, 94, 116, 123, 153, 156–158, 165, 169, 172, 183, 186, 188, 208, 209, 216, 229, 234, 239, 246, 296, 304, 305, and 308. Critical residues are missing at aa positions 166, 187, 214, and 215, while important residues are missing at aa positions 44, 121, 149, 173, 174, 212, 231, 232, and 284. "Critical residues" are those residues that are recognized as important for activity and are highly conserved in known kinases. "Important residues" are those residues generally conserved among kinases.

The 12832 protein shares similarity with several protein kinases. Dendogram analysis of this gene indicates it shares closest homology with C. elegans tyrosine kinase (C.ele. Tyr. Kinase; GenBank Accession Number AAC47047; SEQ ID NO: 29). The 12832 protein shares approximately 26% identity with this protein kinase receptor as determined by pairwise alignment (see Needleman and Wunsch (1970) J. Mol. Biol. 48:444).

A plasmid containing the 12832 cDNA insert was deposited with American Type Culture Collection (ATCC), 10801 University Boulevard, Manassas, Va., on Aug, 10, 2000, and assigned Accession Number PTA-2342. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. '112.

Preferred kinase-like polypeptides of the present invention have an amino acid sequence sufficiently identical to the amino acid sequence of SEQ ID NO:2. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, 65%, 70% identity, preferably 75% or 80%, identity, more preferably 85% or 90%, and most preferably 91%, 92%, 93%, 94%, 95%, 96%, 97%, 98% or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to kinase-like nucleic acid molecules of the invention. BLAST protein searches can be performed with the XBLAST program, score=50, wordlength=3, to obtain amino acid sequences homologous to kinase-like protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. (see the website maintained by National Center for Biotechnology Information, Bethesda, Md., USA). Another preferred, non-limiting example of a mathematical algorithm utilized for the comparison of sequences is the algorithm of Myers and Miller (1988) *CABIOS* 4:11–17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

Accordingly, another embodiment of the invention features isolated kinase-like proteins and polypeptides having a kinase-like protein activity. As used interchangeably herein, a "kinase-like protein activity", "biological activity of a kinase-like protein", or "functional activity of a kinase-like protein" refers to an activity exerted by a kinase-like protein, polypeptide, or nucleic acid molecule on a kinase-like responsive cell as determined in vivo, or in vitro, according to standard assay techniques. A kinase-like activity can be a direct activity, such as an association with or an enzymatic activity on a second protein, or an indirect activity, such as a cellular signaling activity mediated by interaction of the kinase-like protein with a second protein. In a preferred embodiment, kinase-like activity includes at least one or more of the following activities: (1) modulating (stimulating and/or enhancing or inhibiting) cellular proliferation, growth and/or metabolism (e.g. in those cells in which the sequence is expressed, including, lymph node, tonsil, thymus, skeletal muscle, liver, colon, heart, lung, brain, testis, skin, fetal heart, fetal liver, immune cells including Th1, Th2, T cells, natural killer cells, lymphocytes, leukocytes, blod marrow, etc.); (2) the regulation of transmission of signals from cellular receptors, e.g., growth factor receptors; (3) the modulation of the entry of cells into mitosis; (4) the modulation of cellular differentiation; (5) the modulation of cell death; and (6) the regulation of cytoskeleton function, e.g., actin bundling.

An "isolated" or "purified" kinase-like nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated kinase-like nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A kinase-like protein that is substantially free of cellular material includes preparations of kinase-like protein having less than about 30%, 20%, 10%, or 5% (by dry weight) of non-kinase-like protein (also referred to herein as a "contaminating protein"). When the kinase-like protein or biologically active portion thereof is recombinantly produced, preferably, culture medium represents less than about 30%, 20%, 10%, or 5% of the volume of the protein preparation. When kinase-like protein is produced by chemical synthesis, preferably the protein preparations have less than about 30%, 20%, 10%, or 5% (by dry weight) of chemical precursors or non-kinase-like chemicals.

Various aspects of the invention are described in further detail in the following subsections.

I. Isolated Nucleic Acid Molecules

One aspect of the invention pertains to isolated nucleic acid molecules comprising nucleotide sequences encoding kinase-like proteins and polypeptides or biologically active portions thereof, as well as nucleic acid molecules sufficient for use as hybridization probes to identify kinase-like-encoding nucleic acids (e.g., kinase-like mRNA) and fragments for use as PCR primers for the amplification or mutation of kinase-like nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the kinase-like proteins of the present invention include sequences set forth in SEQ ID NO:1, the nucleotide sequence of the cDNA insert of the plasmid deposited with the ATCC as Accession Number PTA-2342 (the "cDNA of ATCC PTA-2342"), and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the kinase-like protein encoded by these nucleotide sequences is set forth in SEQ ID NO:2. The invention also encompasses nucleic acid molecules comprising nucleotide sequences encoding partial-length kinase-like proteins, including the sequence set forth in SEQ ID NO:1, and complements thereof.

Nucleic acid molecules that are fragments of these kinase-like nucleotide sequences are also encompassed by the present invention. By "fragment" is intended a portion of the nucleotide sequence encoding a kinase-like protein. A fragment of a kinase-like nucleotide sequence may encode a biologically active portion of a kinase-like protein, or it may be a fragment that can be used as a hybridization probe or PCR primer using methods disclosed below. A biologically active portion of a kinase-like protein can be prepared by isolating a portion of one of the 12832 nucleotide sequences of the invention, expressing the encoded portion of the kinase-like protein (e.g., by recombinant expression in vitro), and assessing the activity of the encoded portion of the kinase-like protein. Nucleic acid molecules that are fragments of a kinase-like nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1500 nucleotides, or up to the number of nucleotides present in a full-length kinase-like nucleotide sequence disclosed herein (for example, 1586 nucleotides for SEQ ID NO:1) depending on the intended use.

It is understood that isolated fragments include any contiguous sequence not disclosed prior to the invention as well as sequences that are substantially the same and which are not disclosed. Accordingly, if an isolated fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences.

A fragment of a kinase-like nucleotide sequence that encodes a biologically active portion of a kinase-like protein of the invention will encode at least about 15, 25, 30, 50, 75, 100, 125, 150, 175, 200, 250, or 300 contiguous amino acids, or up to the total number of amino acids present in a full-length kinase-like protein of the invention (for example, 322 amino acids for SEQ ID NO:2). Fragments of a kinase-like nucleotide sequence that are useful as hybridization probes for PCR primers generally need not encode a biologically active portion of a kinase-like protein.

Nucleic acid molecules that are variants of the kinase-like nucleotide sequences disclosed herein are also encompassed by the present invention. "Variants" of the kinase-like nucleotide sequences include those sequences that encode the kinase-like proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the kinase-like proteins disclosed in the present invention as discussed below. Generally, nucleotide sequence variants of the invention will have at least about 45%, 55%, 65%, 70%, 75%, 80%, 85%, 90%, 91%, 92%, 93%, 94%, 95%, 96%, 97%, 98%, or 99% identity to a particular nucleotide sequence disclosed herein. A variant kinase-like nucleotide sequence will encode a kinase-like protein that has an amino acid sequence having at least about 45%, 55%, 65%, 70%, 75%, 80%, 85%, 90%, 91%, 92%, 93%, 94%, 95%, 96%, 97%, 98% or 99% identity to the amino acid sequence of a kinase-like protein disclosed herein.

In addition to the kinase-like nucleotide sequences shown in SEQ ID NO:1 and the nucleotide sequence of the cDNA of ATCC PTA-2342 it will be appreciated by those skilled in the art that DNA sequence polymorphisms that lead to changes in the amino acid sequences of kinase-like proteins may exist within a population (e.g., the human population).

Such genetic polymorphism in a kinase-like gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding a kinase-like protein, preferably a mammalia kinase-like protein. As used herein, the phrase "allelic variant" refers to a nucleotide sequence that occurs at a kinase-like locus or to a polypeptide encoded by the nucleotide sequence. Such natural allelic variations can typically result in 1–5% variance in the nucleotide sequence of the kinase-like gene. Any and all such nucleotide variations and resulting amino acid polymorphisms or variations in a kinase-like sequence that are the result of natural allelic variation and that do not alter the functional activity of kinase-like proteins are intended to be within the scope of the invention.

Moreover, nucleic acid molecules encoding kinase-like proteins from other species (kinase-like homologues), which have a nucleotide sequence differing from that of the kinase-like sequences disclosed herein, are intended to be within the scope of the invention. For example, nucleic acid molecules corresponding to natural allelic variants and homologues of the huma kinase-like cDNA of the invention can be isolated based on their identity to the huma kinase-like nucleic acid disclosed herein using the human cDNA, or a portion thereof, as a hybridization probe according to standard hybridization techniques under stringent hybridization conditions as disclosed below.

In addition to naturally-occurring allelic variants of the kinase-like sequences that may exist in the population, the skilled artisan will further appreciate that changes can be introduced by mutation into the nucleotide sequences of the invention thereby leading to changes in the amino acid sequence of the encoded kinase-like proteins, without altering the biological activity of the kinase-like proteins. Thus, an isolated nucleic acid molecule encoding a kinase-like protein having a sequence that differs from that of SEQ ID NO:2 can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a kinase-like protein (e.g., the sequence of SEQ ID NO:2) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing in a conserved domain, such as the critical eukaryotic protein kinase domain.

Alternatively, variant kinase-like nucleotide sequences can be made by introducing mutations randomly along all or part of a kinase-like coding sequence, such as by saturation mutagenesis, and the resultant mutants can be screened for kinase-like biological activity to identify mutants that retain activity. Following mutagenesis, the encoded protein can be expressed recombinantly, and the activity of the protein can be determined using standard assay techniques.

Thus the nucleotide sequences of the invention include the sequences disclosed herein as well as fragments and variants thereof. The kinase-like nucleotide sequences of the invention, and fragments and variants thereof, can be used as probes and/or primers to identify and/or clone kinase-like homologues in other cell types, e.g., from other tissues, as well as kinase-like homologues from other mammals. Such probes can be used to detect transcripts or genomic sequences encoding the same or identical proteins. These probes can be used as part of a diagnostic test kit for identifying cells or tissues that misexpress a kinase-like protein, such as by measuring levels of a kinase-like-encoding nucleic acid in a sample of cells from a subject, e.g., detecting kinase-like mRNA levels or determining whether a genomic kinase-like gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, N.Y.). Kinase-like nucleotide sequences isolated based on their sequence identity to the kinase-like nucleotide sequences set forth herein or to fragments and variants thereof are encompassed by the present invention.

In a hybridization method, all or part of a known kinase-like nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known kinase-like nucleotide sequence disclosed herein. Degenerate primers designed on the basis of conserved nucleotides or amino acid residues in a known kinase-like nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of a kinase-like nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified kinase-like nucleic acid molecule hybridizes under stringent conditions to a probe that is a nucleic acid molecule comprising one of the kinase-like nucleotide sequences of the invention or a fragment thereof. In another embodiment, the previously unknown kinase-like nucleic acid molecule is at least about 300, 325, 350, 375, 400, 425, 450, 500, 550, 600, 650, 700, 800, 900, 1000, 2,000, 3,000, 4,000 or 5,000 nucleotides in length and hybridizes under stringent conditions to a probe that is a nucleic acid molecule comprising one of the kinase-like nucleotide sequences disclosed herein or a fragment thereof.

Accordingly, in another embodiment, an isolated previously unknown kinase-like nucleic acid molecule of the invention is at least about 300, 325, 350, 375, 400, 425, 450, 500, 550, 600, 650, 700, 800, 900, 1000, 1,100, 1,200, 1,300, or 1,400 nucleotides in length and hybridizes under stringent conditions to a probe that is a nucleic acid molecule comprising one of the nucleotide sequences of the invention, preferably the coding sequence set forth in SEQ ID NO:1, the cDNA of ATCC PTA-2342 or a complement, fragment, or variant thereof.

As used herein, the term "hybridizes under stringent conditions" is intended to describe conditions for hybridization and washing under which nucleotide sequences having at least about 60%, 65%, 70%, preferably 75% identity to each other typically remain hybridized to each other. Such stringent conditions are known to those skilled in the art and can be found in *Current Protocols in Molecular Biology* (John Wiley & Sons, New York (1989)), 6.3.1–6.3.6. A preferred, non-limiting example of stringent hybridization conditions is hybridization in 6× sodium chloride/sodium citrate (SSC) at about 45° C., followed by one or more washes in 0.2×SSC, 0.1% SDS at 50–65° C. In another preferred embodiment, stringent conditions comprise hybridization in 6×SSC at 42° C., followed by washing with 1×SSC at 55° C. Preferably, an isolated nucleic acid molecule that hybridizes under stringent conditions to a kinase-like sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

Thus, in addition to the kinase-like nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the kinase-like nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire kinase-like coding strand, or to only a portion thereof, e.g., all or part of the protein coding region (or open reading frame). An antisense nucleic acid molecule can be antisense to a noncoding region of the coding strand of a nucleotide sequence encoding a kinase-like protein. The noncoding regions are the 5' and 3' sequences that flank the coding region and are not translated into amino acids.

Given the coding-strand sequence encoding a kinase-like protein disclosed herein (e.g., SEQ ID NO:1), antisense nucleic acids of the invention can be designed according to the rules of Watson and Crick base pairing. The antisense nucleic acid molecule can be complementary to the entire coding region of kinase-like mRNA, but more preferably is an oligonucleotide that is antisense to only a portion of the coding or noncoding region of kinase-like mRNA. For example, the antisense oligonucleotide can be complementary to the region surrounding the translation start site of kinase-like mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

When used therapeutically, the antisense nucleic acid molecules of the invention are typically administered to a subject or generated in situ such that they hybridize with or bind to cellular mRNA and/or genomic DNA encoding a kinase-like protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585–591)) can be used to catalytically cleave kinase-like mRNA transcripts to thereby inhibit translation of kinase-like mRNA. A ribozyme having specificity for a kinase-like-encoding nucleic acid can be designed based upon the nucleotide sequence of a kinase-like cDNA disclosed herein (e.g., SEQ ID NO:1).

See, e.g., Cech et al., U.S. Pat. No. 4,987,071; and Cech et al., U.S. Pat. No. 5,116,742. Alternatively, kinase-like mRNA can be used to select a catalytic RNA having a specific ribonuclease activity from a pool of RNA molecules. See, e.g., Bartel and Szostak (1993) *Science* 261: 1411–1418.

The invention also encompasses nucleic acid molecules that form triple helical structures. For example, kinase-like gene expression can be inhibited by targeting nucleotide sequences complementary to the regulatory region of the kinase-like protein (e.g., the kinase-like promoter and/or enhancers) to form triple helical structures that prevent transcription of the kinase-like gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described, for example, in Hyrup et al. (1996), supra; Perry-O'Keefe et al. (1996) *Proc. Natl. Acad. Sci. USA* 93:14670.

PNAs of a kinase-like molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping; as artificial restriction enzymes when used in combination with other enzymes, e.g., S1 nucleases (Hyrup (1996), supra); or as probes or primers for DNA sequence and hybridization (Hyrup (1996), supra; Perry-O'Keefe et al. (1996), supra).

In another embodiment, PNAs of a kinase-like molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357–63; Mag et al. (1989) *Nucleic Acids Res.* 17:5973; and Peterson et al. (1975) *Bioorganic Med. Chem. Lett.* 5:1119.

II. Isolated Kinase-like Proteins and Anti-Kinase-like Antibodies

Huma kinase-like proteins are also encompassed within the present invention. By "kinase-like protein" is intended a protein having the amino acid sequence set forth in SEQ ID NO: 2, as well as fragments, biologically active portions, and variants thereof.

"Fragments" or "biologically active portions" include polypeptide fragments suitable for use as immunogens to raise anti-kinase-like antibodies. Fragments include peptides comprising amino acid sequences sufficiently identical to or derived from the amino acid sequence of a kinase-like protein, or partial-length protein, of the invention and exhibiting at least one activity of a kinase-like protein, but which include fewer amino acids than the full-length (SEQ ID NO:2). Typically, biologically active portions comprise a domain or motif with at least one activity of the kinase-like protein. A biologically active portion of a kinase-like protein can be a polypeptide which is, for example, 10, 25, 50, 100 or more amino acids in length. Such biologically activeportions can be prepared by recombinant techniques and evaluated for one or more of the functional activities of a native kinase-like protein. By "variants" is intended proteins or polypeptides having an amino acid sequence that is at least about 45%, 55%, 65%, 70%, preferably about 75%, 80%, 85%, 90%, 91%, 92%, 93%, 94%, 95%, 96%, 97%, 98%, 99% identical to the amino acid sequence of SEQ ID NO:2. Variants also include polypeptides encoded by the cDNA insert of the plasmid deposited with ATCC as Accession Number PTA-2342, or polypeptides encoded by a nucleic acid molecule that hybridizes to the nucleic acid molecule of SEQ ID NO:1, or a complement thereof, under stringent conditions. Such variants generally retain the functional activity of the kinase-like proteins of the invention. Variants include polypeptides that differ in amino acid sequence due to natural allelic variation or mutagenesis.

The invention also provides kinase-like chimeric or fusion proteins. As used herein, a kinase-like "chimeric protein" or "fusion protein" comprises a kinase-like polypeptide operably linked to a non-kinase-like polypeptide. A "kinase-like polypeptide" refers to a polypeptide having an amino acid sequence corresponding to a kinase-like protein, whereas a "non-kinase-like polypeptide" refers to a polypeptide having an amino acid sequence corresponding to a protein that is not substantially identical to the kinase-like protein, e.g., a protein that is different from the kinase-like protein and which is derived from the same or a different organism. Within a kinase-like fusion protein, the kinase-like polypeptide can correspond to all or a portion of a kinase-like protein, preferably at least one biologically active portion of a kinase-like protein. Within the fusion protein, the term "operably linked" is intended to indicate that the kinase-like polypeptide and the non-kinase-like polypeptide are fused in-frame to each other. The non-kinase-like polypeptide can be fused to the N-terminus or C-terminus of the kinase-like polypeptide.

One useful fusion protein is a GST-kinase-like fusion protein in which the kinase-like sequences are fused to the C-terminus of the GST sequences. Such fusion proteins can facilitate the purification of recombinant kinase-like proteins.

In yet another embodiment, the fusion protein is a kinase-like-immunoglobulin fusion protein in which all or part of a kinase-like protein is fused to sequences derived from a member of the immunoglobulin protein family. The kinase-like-immunoglobulin fusion proteins of the invention can be incorporated into pharmaceutical compositions and administered to a subject to inhibit an interaction between a kinase-like ligand and a kinase-like protein on the surface of a cell, thereby suppressing kinase-like-mediated signal transduction in vivo. The kinase-like-immunoglobulin fusion proteins can be used to affect the bioavailability of a kinase-like cognate ligand. Inhibition of the kinase-like ligand/kinase-like interaction may be useful therapeutically, both for treating proliferative and differentiative disorders and for modulating (e.g., promoting or inhibiting) cell survival. Moreover, the kinase-like immunoglobulin fusion proteins of the invention can be used as immunogens to produce anti-kinase-like antibodies in a subject, to purify kinase-like ligands, and in screening assays to identify molecules that inhibit the interaction of a kinase-like protein with a kinase-like ligand.

Preferably, a kinase-like chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, a kinase-like-encoding nucleic acid can be cloned into a commercially available expression vector such that it is linked in-frame to an existing fusion moiety.

Variants of the kinase-like proteins can function as either kinase-like agonists (mimetics) or as kinase-like antagonists. Variants of the kinase-like protein can be generated by mutagenesis, e.g., discrete point mutation or truncation of the kinase-like protein. An agonist of the kinase-like protein can retain substantially the same, or a subset, of the biological activities of the naturally occurring form of the kinase-like protein. An antagonist of the kinase-like protein can inhibit one or more of the activities of the naturally occurring form of the kinase-like protein by, for example, competitively binding to a downstream or upstream member of a cellular signaling cascade that includes the kinase-like protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the kinase-like proteins.

Variants of a kinase-like protein that function as either kinase-like agonists or as kinase-like antagonists can be identified by screening combinatorial libraries of mutants, e.g., truncation mutants, of a kinase-like protein for kinase-like protein agonist or antagonist activity. In one embodiment, a variegated library of kinase-like variants is generated by combinatorial mutagenesis at the nucleic acid level and is encoded by a variegated gene library. A variegated library of kinase-like variants can be produced by, for example, enzymatically ligating a mixture of synthetic oligonucleotides into gene sequences such that a degenerate set of potential kinase-like sequences is expressible as individual polypeptides, or alternatively, as a set of larger fusion proteins (e.g., for phage display) containing the set of kinase-like sequences therein. There are a variety of methods that can be used to produce libraries of potential kinase-like variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential kinase-like sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a kinase-like protein coding sequence can be used to generate a variegated population of kinase-like fragments for screening and subsequent selection of variants of a kinase-like protein. In one embodiment, a library of coding sequence fragments can be generated by treating a double-stranded PCR fragment of a kinase-like coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the kinase-like protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of kinase-like proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify kinase-like variants (Arkin and Yourvan (1992) *Proc. Natl. Acad. Sci. USA* 89:7811–7815; Delgrave et al. (1993) *Protein Engineering* 6(3):327–331).

An isolated kinase-like polypeptide of the invention can be used as an immunogen to generate antibodies that bind kinase-like proteins using standard techniques for polyclonal and monoclonal antibody preparation. The full-length kinase-like protein can be used or, alternatively, the invention provides antigenic peptide fragments of kinase-like proteins for use as immunogens. The antigenic peptide of a kinase-like protein comprises at least 8, preferably 10, 15, 20, or 30 amino acid residues of the amino acid sequence shown in SEQ ID NO:2 and encompasses an epitope of a kinase-like protein such that an antibody raised against the peptide forms a specific immune complex with the kinase-like protein. Preferred epitopes encompassed by the antigenic peptide are regions of a kinase-like protein that are located on the surface of the protein, e.g., hydrophilic regions.

Accordingly, another aspect of the invention pertains to anti-kinase-like polyclonal and monoclonal antibodies that bind a kinase-like protein. Polyclonal anti-kinase-like antibodies can be prepared by immunizing a suitable subject (e.g., rabbit, goat, mouse, or other mammal) with a kinase-like immunogen. The anti-kinase-like antibody titer in the immunized subject can be monitored over time by standard techniques, such as with an enzyme linked immunosorbent assay (ELISA) using immobilized kinase-like protein. At an appropriate time after immunization, e.g., when the anti-kinase-like antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.*, 54:387–402).

Alternative to preparing monoclonal antibody-secreting hybridomas, a monoclonal anti-kinase-like antibody can be identified and isolated by screening a recombinant combinatorial immunoglobulin library (e.g., an antibody phage display library) with a kinase-like protein to thereby isolate immunoglobulin library members that bind the kinase-like protein. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant anti-kinase-like antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86/101533 and WO 87/02671; European Patent Application Nos. 184,187, 171,496, 125,023, and 173,494; U.S. Pat. Nos. 4,816,567 and 5,225,539; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559); Morrison (1985) *Science* 229:1202–1207; Oi et al. (1986) *Bio/Techniques* 4:214; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Fremont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

An anti-kinase-like antibody (e.g., monoclonal antibody) can be used to isolate kinase-like proteins by standard techniques, such as affinity chromatography or immunoprecipitation. An anti-kinase-like antibody can facilitate the purification of natural kinase-like protein from cells and of recombinantly produced kinase-like protein expressed in host cells. Moreover, an anti-kinase-like antibody can be used to detect kinase-like protein (e.g., in a cellular lysate or cell supernatant) in order to evaluate the abundance and pattern of expression of the kinase-like protein. Anti-kinase-like antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^3H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84:Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding a kinase-like protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., kinase-like proteins, mutant forms of kinase-like proteins, fusion proteins, etc.).

The recombinant expression vectors of the invention can be designed for expression of kinase-like protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301–315) and pET 11d (Studier et al. (1990) in *Gene Expression Technology: Methods in Enzymology* 185 (Academic Press, San Diego, Calif.), pp. 60–89). Strategies to maximize recombinant protein expression in *E. coli* can be found in Gottesman (1990) in *Gene Expression Technology: Methods in Enzymology* 185 (Academic Press, CA), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39)); yeast cells (examples of vectors for expression in yeast *S. cereivisiae* include pYepSec1 (Baldari et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (e.g., liver-specific promoter; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Patent Publication No. 264,166). Developmentally-regulated promoters are also encompassed, for example the murine hox homeobox promoters (Kessel and Gruss (1990) *Science* 249:374–379), the α-fetoprotein promoter (Campes and Tilghman (1989) *Genes Dev.* 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to kinase-like mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics*, Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboraty Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest.

Preferred selectable markers include those which confer resistance to drugs, such as G418, hygromycin, and methotrexate. Nucleic acid encoding a selectable marker can be introduced into a host cell on the same vector as that encoding a kinase-like protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) kinase-like protein. Accordingly, the invention further provides methods for producing kinase-like protein using the host cells of the invention. In one embodiment, the method comprises culturing the host cell of the invention, into which a recombinant expression vector encoding a kinase-like protein has been introduced, in a suitable medium such that kinase-like protein is produced. In another embodiment, the method further comprises isolating kinase-like protein from the medium or the host cell.

The host cells of the invention can also be used to produce nonhuman transgenic animals. For example, in one embodiment, a host cell of the invention is a fertilized oocyte or an embryonic stem cell into which kinase-like-coding sequences have been introduced. Such host cells can then be used to create nonhuman transgenic animals in which exogenous kinase-like sequences have been introduced into their genome or homologous recombinant animals in which endogenous kinase-like sequences have been altered. Such animals are useful for studying the function and/or activity of kinase-like genes and proteins and for identifying and/or evaluating modulators of kinase-like activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous kinase-like gene has been altered by homologous recombination between the endogenous gene and an exogenous DNA molecule introduced into a cell of the animal, e.g., an embryonic cell of the animal, prior to development of the animal.

A transgenic animal of the invention can be created by introducing kinase-like-encoding nucleic acid into the male pronuclei of a fertilized oocyte, e.g., by microinjection, retroviral infection, and allowing the oocyte to develop in a pseudopregnant female foster animal. The kinase-like cDNA sequence can be introduced as a transgene into the genome of a nonhuman animal. Alternatively, a homologue of the mouse kinase-like gene can be isolated based on hybridization and used as a transgene. Intronic sequences and polyadenylation signals can also be included in the transgene to increase the efficiency of expression of the transgene. A tissue-specific regulatory sequence(s) can be operably linked to the kinase-like transgene to direct expression of kinase-like protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the kinase-like transgene in its genome and/or expression of kinase-like mRNA in tissues or cells of the animals. A transgenic founder animal can then be used to breed additional animals carrying the transgene. Moreover, transgenic animals carrying a transgene encoding kinase-like gene can further be bred to other transgenic animals carrying other transgenes.

To create a homologous recombinant animal, one prepares a vector containing at least a portion of a kinase-like gene or a homolog of the gene into which a deletion, addition, or substitution has been introduced to thereby alter, e.g., functionally disrupt, the kinase-like gene. In a preferred embodiment, the vector is designed such that, upon homologous recombination, the endogenous kinase-like gene is functionally disrupted (i.e., no longer encodes a functional protein; also referred to as a "knock out" vector). Alternatively, the vector can be designed such that, upon homologous recombination, the endogenous kinase-like gene is mutated or otherwise altered but still encodes functional protein (e.g., the upstream regulatory region can be altered to thereby alter the expression of the endogenous kinase-like protein). In the homologous recombination vector, the altered portion of the kinase-like gene is flanked at its 5' and 3' ends by additional nucleic acid of the kinase-like gene to allow for homologous recombination to occur between the exogenous kinase-like gene carried by the vector and an endogenous kinase-like gene in an embryonic stem cell. The additional flanking kinase-like nucleic acid is of sufficient length for successful homologous recombination with the endogenous gene. Typically, several kilobases of flanking DNA (at both the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced kinase-like gene has homologously recombined with the endogenous kinase-like gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science*

251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) Nature 385:810–813 and PCT Publication Nos. WO 97/07668 and WO 97/07669.

IV. Pharmaceutical Compositions

The kinase-like nucleic acid molecules, kinase-like proteins, and anti-kinase-like antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., a kinase-like protein or anti-kinase-like antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 μg/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 μg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express kinase-like protein (e.g., via a recombinant expression vector in a host cell in gene therapy applications), to detect kinase-like mRNA (e.g., in a biological sample) or a genetic lesion in a kinase-like gene, and to modulate kinase-like activity. In addition, the kinase-like proteins can be used to screen drugs or compounds that modulate cellular growth and/or metabolism as well as to treat disorders characterized by insufficient or excessive production of kinase-like protein or production of kinase-like protein forms that have decreased or aberrant activity compared to kinase-like wild type protein. In addition, the anti-kinase-like antibodies of the invention can be used to detect and isolate kinase-like proteins and modulate kinase-like activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to kinase-like proteins or have a stimulatory or inhibitory effect on, for example, kinase-like expression or kinase-like activity.

The test compounds of the present invention can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869), or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Determining the ability of the test compound to bind to the kinase-like protein can be accomplished, for example, by coupling the test compound with a radioisotope or enzymatic label such that binding of the test compound to the kinase-like protein or biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the kinase-like protein to bind to or interact with a kinase-like target molecule. By "target molecule" is intended a molecule with which a kinase-like protein binds or interacts in nature. In a preferred embodiment, the ability of the kinase-like protein to bind to or interact with a kinase-like target molecule can be determined by monitoring the activity of the target molecule. Also for example, the activity of the target molecule can be monitored by detecting induction of a cellular second messenger of the target (e.g., intracellular $Ca^{+2}$, diacylglycerol, IP3, etc.), detecting catalytic/enzymatic activity of the target on an appropriate substrate, detecting the induction of a reporter gene (e.g., a kinase-responsive regulatory element operably linked to a nucleic acid encoding a detectable marker, e.g., luciferase), or detecting a cellular response, for example, cellular differentiation or cell proliferation.

In yet another embodiment, an assay of the present invention is a cell-free assay comprising contacting a kinase-like protein or biologically active portion thereof with a test compound and determining the ability of the test compound to bind to the kinase-like protein or biologically active portion thereof. Binding of the test compound to the kinase-like protein can be determined either directly or indirectly as described above. In a preferred embodiment, the assay includes contacting the kinase-like protein or biologically active portion thereof with a known compound that binds kinase-like protein to form an assay mixture, contacting the assay mixture with a test compound, and determining the ability of the test compound to preferentially bind to kinase-like protein or biologically active portion thereof as compared to the known compound.

In another embodiment, an assay is a cell-free assay comprising contacting kinase-like protein or biologically active portion thereof with a test compound and determining the ability of the test compound to modulate (e.g., stimulate or inhibit) the activity of the kinase-like protein or biologically active portion thereof. Determining the ability of the test compound to modulate the activity of a kinase-like protein can be accomplished, for example, by determining the ability of the kinase-like protein to bind to a kinase-like target molecule as described above for determining direct binding. In an alternative embodiment, determining the ability of the test compound to modulate the activity of a kinase-like protein can be accomplished by determining the ability of the kinase-like protein to further modulate a kinase-like target molecule. For example, the catalytic/enzymatic activity of the target molecule on an appropriate substrate can be determined as previously described.

In yet another embodiment, the cell-free assay comprises contacting the kinase-like protein or biologically active portion thereof with a known compound that binds a kinase-like protein to form an assay mixture, contacting the assay mixture with a test compound, and determining the ability of the test compound to preferentially bind to or modulate the activity of a kinase-like target molecule.

In the above-mentioned assays, it may be desirable to immobilize either a kinase-like protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/kinase-like fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or kinase-like protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of kinase-like binding or activity determined using standard techniques.

Other techniques for immobilizing proteins on matrices can also be used in the screening assays of the invention. For example, either kinase-like protein or its target molecule can be immobilized utilizing conjugation of biotin and streptavidin. Biotinylated kinase-like molecules or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with a kinase-like protein or target molecules but which do not interfere with binding of the kinase-like protein to its target molecule can be derivatized to the wells of the plate, and unbound target or kinase-like protein trapped in the wells by antibody conjugation. Methods for detecting such complexes, in addition to those described above for the GST-immobilized complexes, include immunodetection of complexes using antibodies reactive with the kinase-like protein or target molecule, as well as enzyme-linked assays that rely on detecting an enzymatic activity associated with the kinase-like protein or target molecule.

In another embodiment, modulators of kinase-like expression are identified in a method in which a cell is contacted with a candidate compound and the expression of kinase-like mRNA or protein in the cell is determined relative to expression of kinase-like mRNA or protein in a cell in the absence of the candidate compound. When expression is greater (statistically significantly greater) in the presence of the candidate compound than in its absence, the candidate compound is identified as a stimulator of kinase-like mRNA or protein expression. Alternatively, when expression is less (statistically significantly less) in the presence of the candidate compound than in its absence, the candidate compound is identified as an inhibitor of kinase-like mRNA or protein expression. The level of kinase-like mRNA or protein expression in the cells can be determined by methods described herein for detecting kinase-like mRNA or protein.

In yet another aspect of the invention, the kinase-like proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with kinase-like protein ("kinase-like-binding proteins" or "kinase-like-bp") and modulate kinase-like activity. Such kinase-like-binding proteins are also likely to be involved in the propagation of signals by the kinase-like proteins as, for example, upstream or downstream elements of the kinase-like pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial kinase-like gene sequences of the invention can be used to map their respective kinase-like genes on a chromosome, thereby facilitating the location of gene regions associated with genetic disease. Computer analysis of kinase-like sequences can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the kinase-like sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919–924). Somatic cell hybrids containing only fragments of human chromosomes can also be produced by using human chromosomes with translocations and deletions.

Other mapping strategies that can similarly be used to map a kinase-like sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma eta a. (1988) *Human Chromosomes: A Manual of Basic Techniques* (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Another strategy to map the chromosomal location of kinase-like genes uses kinase-like polypeptides and fragments and sequences of the present invention and antibodies specific thereto. This mapping can be carried out by specifically detecting the presence of a kinase-like polypeptide in members of a panel of somatic cell hybrids between cells of a first species of animal from which the protein originates and cells from a second species of animal, and then determining which somatic cell hybrid(s) expresses the polypeptide and noting the chromosomes(s) from the first species of animal that it contains. For examples of this technique, see Pajunen et al. (1988) *Cytogenet. Cell. Genet.* 47:37–41 and Van Keuren et al. (1986) *Hum. Genet.* 74:34–40. Alternatively, the presence of a kinase-like polypeptide in the somatic cell hybrids can be determined by assaying an activity or property of the polypeptide, for example, enzymatic activity, as described in Bordelon-Riser et al. (1979) *Somatic Cell Genetics* 5:597–613 and Owerbach et al. (1978) *Proc. Natl. Acad. Sci. USA* 75:5640–5644.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with the kinase-like gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The kinase-like sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described, e.g., in U.S. Pat. No. 5,272,057).

Furthermore, the sequences of the present invention can be used to provide an alternative technique for determining the actual base-by-base DNA sequence of selected portions of an individual's genome. Thus, the kinase-like sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The kinase-like sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of SEQ ID NO:1 can comfortably provide positive individual identification with a panel of perhaps 10 to 1,000 primers that each yield a noncoding amplified sequence of 100 bases. If a predicted coding sequence, such as that in SEQ ID NO:2, is used, a more appropriate number of primers for positive individual identification would be 500 to 2,000.

3. Use of Partial Kinase-like Sequences in Forensic Biology

DNA-based identification techniques can also be used in forensic biology. In this manner, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the kinase-like sequences or portions thereof, e.g., fragments derived from the noncoding regions of SEQ ID NO:1 having a length of at least 20 or 30 bases.

The kinase-like sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such kinase-like probes, can be used to identify tissue by species and/or by organ type.

In a similar fashion, these reagents, e.g., kinase-like primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting kinase-like protein and/or nucleic acid expression as well as kinase-like activity, in the context of a biological sample. An exemplary method for detecting the presence or absence of kinase-like proteins in a biological sample involves obtaining a biological sample from a test subject and contacting the biological sample with a compound or an agent capable of detecting kinase-like protein or nucleic acid (e.g., mRNA, genomic DNA) that encodes kinase-like protein such that the presence of kinase-like protein is detected in the biological sample. Results obtained with a biological sample from the test subject may be compared to results obtained with a biological sample from a control subject.

A preferred agent for detecting kinase-like mRNA or genomic DNA is a labeled nucleic acid probe capable of hybridizing to kinase-like mRNA or genomic DNA. The nucleic acid probe can be, for example, a full-length kinase-like nucleic acid, such as the nucleic acid of SEQ ID NO:1, or a portion thereof, such as a nucleic acid molecule of at least 15, 30, 50, 100, 250, or 500 nucleotides in length and sufficient to specifically hybridize under stringent conditions to kinase-like mRNA or genomic DNA. Other suitable probes for use in the diagnostic assays of the invention are described herein.

A preferred agent for detecting kinase-like protein is an antibody capable of binding to kinase-like protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect kinase-like mRNA, protein, or genomic DNA in a biological sample in vitro as well as in vivo. For example, in vitro techniques for detection of kinase-like mRNA include Northern hybridizations and in situ hybridizations. In vitro techniques for detection of kinase-like protein include enzyme linked immunosorbent assays (ELISAs), Western blots, immunoprecipitations, and immunofluorescence. In vitro techniques for detection of kinase-like genomic DNA include Southern hybridizations. Furthermore, in vivo techniques for detection of kinase-like protein include introducing into a subject a labeled anti-kinase-like antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. Biological samples may be obtained from blood, serum, cells, or tissue of a subject.

The invention also encompasses kits for detecting the presence of kinase-like proteins in a biological sample (a test sample). Such kits can be used to determine if a subject is suffering from or is at increased risk of developing a disorder associated with aberrant expression of kinase-like protein. For example, the kit can comprise a labeled compound or agent capable of detecting kinase-like protein or mRNA in a biological sample and means for determining the amount of a kinase-like protein in the sample (e.g., an anti-kinase-like antibody or an oligonucleotide probe that binds to DNA encoding a kinase-like protein, e.g., SEQ ID NO:1). Kits can also include instructions for observing that the tested subject is suffering from or is at risk of developing a disorder associated with aberrant expression of kinase-like sequences if the amount of kinase-like protein or mRNA is above or below a normal level.

For antibody-based kits, the kit can comprise, for example: (1) a first antibody (e.g., attached to a solid support) that binds to kinase-like protein; and, optionally, (2) a second, different antibody that binds to kinase-like protein or the first antibody and is conjugated to a detectable agent. For oligonucleotide-based kits, the kit can comprise, for example: (1) an oligonucleotide, e.g., a detectably labeled oligonucleotide, that hybridizes to a kinase-like nucleic acid sequence or (2) a pair of primers useful for amplifying a kinase-like nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of kinase-like proteins.

2. Other Diagnostic Assays

In another aspect, the invention features a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a kinase-like nucleic acid, preferably purified, polypeptide, preferably purified, or antibody, and thereby evaluating the plurality of capture probes. Binding, e.g., in the case of a nucleic acid, hybridization, with a capture probe at an address of the plurality, is detected, e.g., by signal generated from a label attached to the kinase-like nucleic acid, polypeptide, or antibody. The capture probes can be a set of nucleic acids from a selected sample, e.g., a sample of nucleic acids derived from a control or non-stimulated tissue or cell.

The method can include contacting the kinase-like nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of a kinase-like sequence of the invention. Such methods can be used to diagnose a subject, e.g., to evaluate risk for a disease or disorder, to evaluate suitability of a selected treatment for a subject, to evaluate whether a subject has a disease or disorder.

The method can be used to detect single nucleotide polymorphisms (SNPs), as described below.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express a kinase-like polypeptide of the invention or from a cell or subject in which a kinase-like-mediated response has been elicited, e.g., by contact of the cell with a kinase-like nucleic acid or protein of the invention, or administration to the cell or subject a kinase-like nucleic acid or protein of the invention; contacting the array with one or more inquiry probes, wherein an inquiry probe can be a nucleic acid, polypeptide, or antibody (which is preferably other than a kinase-like nucleic acid, polypeptide, or antibody of the invention); providing a two dimensional array having a plurality of addresses, each address of the plurality being positionally distinguishable from each other address of the plurality, and each address of the plurality having a unique capture probe, e.g., wherein the capture probes are from a cell or subject which does not express a kinase-like sequence of the invention (or does not express as highly as in the case of the kinase-like positive plurality of capture probes) or from a cell or subject in which a kinase-like-mediated response has not been elicited (or has been elicited to a lesser extent than in the first sample); contacting the array with one or more inquiry probes (which is preferably other than a kinase-like nucleic acid, polypeptide, or antibody of the invention), and thereby evaluating the plurality of capture probes. Binding, e.g., in the case of a nucleic acid, hybridization, with a capture probe at an address of the plurality, is detected, e.g., by signal generated from a label attached to the nucleic acid, polypeptide, or antibody.

In another aspect, the invention features a method of analyzing a kinase-like sequence of the invention, e.g., analyzing structure, function, or relatedness to other nucleic acid or amino acid sequences. The method includes: providing a kinase-like nucleic acid or amino acid sequence, e.g., the 12832 sequence set forth in SEQ ID NO:1 or a portion thereof; comparing the kinase-like sequence with one or more preferably a plurality of sequences from a collection of sequences, e.g., a nucleic acid or protein sequence database; to thereby analyze the kinase-like sequence of the invention.

The method can include evaluating the sequence identity between a kinase-like sequence of the invention, e.g., the 12832 sequence, and a database sequence. The method can be performed by accessing the database at a second site, e.g., over the internet.

In another aspect, the invention features, a set of oligonucleotides, useful, e.g., for identifying SNP's, or identifying specific alleles of a kinase-like sequence of the invention, e.g., the 12832 sequence. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotides which hybridizes to one allele provides a signal that is distinguishable from an oligonucleotides which hybridizes to a second allele.

3. Prognostic Assays

The methods described herein can furthermore be utilized as diagnostic or prognostic assays to identify subjects having or at risk of developing a disease or disorder associated with kinase-like protein, kinase-like nucleic acid expression, or kinase-like activity. Prognostic assays can be used for prognostic or predictive purposes to thereby prophylactically treat an individual prior to the onset of a disorder characterized by or associated with kinase-like protein, kinase-like nucleic acid expression, or kinase-like activity.

Thus, the present invention provides a method in which a test sample is obtained from a subject, and kinase-like protein or nucleic acid (e.g., mRNA, genomic DNA) is detected, wherein the presence of kinase-like protein or nucleic acid is diagnostic for a subject having or at risk of developing a disease or disorder associated with aberrant kinase-like expression or activity. As used herein, a "test sample" refers to a biological sample obtained from a subject of interest. For example, a test sample can be a biological fluid (e.g., serum), cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease kinase-like activity) to effectively treat a disease or disorder associated with aberrant kinase-like expression or activity. In this manner, a test sample is obtained and kinase-like protein or nucleic acid is detected. The presence of kinase-like protein or nucleic acid is diagnostic for a subject that can be administered the agent to treat a disorder associated with aberrant kinase-like expression or activity.

The methods of the invention can also be used to detect genetic lesions or mutations in a kinase-like gene, thereby determining if a subject with the lesioned gene is at risk for a disorder characterized by aberrant cell proliferation, cell growth, cell cycling and/or differentiation. In preferred embodiments, the methods include detecting, in a sample of cells from the subject, the presence or absence of a genetic lesion or mutation characterized by at least one of an alteration affecting the integrity of a gene encoding a kinase-like-protein, or the misexpression of the kinase-like gene. For example, such genetic lesions or mutations can be detected by ascertaining the existence of at least one of: (1) a deletion of one or more nucleotides from a kinase-like gene; (2) an addition of one or more nucleotides to a kinase-like gene; (3) a substitution of one or more nucleotides of a kinase-like gene; (4) a chromosomal rearrangement of a kinase-like gene; (5) an alteration in the level of a messenger RNA transcript of a kinase-like gene; (6) an aberrant modification of a kinase-like gene, such as of the methylation pattern of the genomic DNA; (7) the presence of a non-wild-type splicing pattern of a messenger RNA transcript of a kinase-like gene; (8) a non-wild-type level of a kinase-like-protein; (9) an allelic loss of a kinase-like gene; and (10) an inappropriate post-translational modification of a kinase-like-protein. As described herein, there are a large number of assay techniques known in the art that can be used for detecting lesions in a kinase-like gene. Any cell type or tissue in which kinase-like proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the kinase-like-gene (see, e.g., Abravaya et al. (1995) *Nucleic Acids Res.* 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a kinase-like gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in a kinase-like molecule can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). In yet another embodiment, any of a variety of sequencing reactions known in the art can be used to directly sequence the kinase-like gene and detect mutations by comparing the sequence of the sample kinase-like gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the kinase-like gene include methods in which protection from cleavage agents is used to detect mismatched bases in RNA/RNA or RNA/DNA heteroduplexes (Myers et al. (1985) *Science* 230:1242). See, also Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in kinase-like cDNAs obtained from samples of cells. See, e.g., Hsu et al. (1994) *Carcinogenesis* 15:1657–1662. According to an exemplary embodiment, a probe based on a kinase-like sequence, e.g., a wild-type kinase-like sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in kinase-like genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnosed patients exhibiting symptoms or family history of a disease or illness involving a kinase-like gene.

4. Pharmacogenomics

Agents, or modulators that have a stimulatory or inhibitory effect on kinase-like activity (e.g., kinase-like gene expression) as identified by a screening assay described herein, can be administered to individuals to treat (prophylactically or therapeutically) disorders associated with aberrant kinase-like activity as well as to modulate the cellular growth, differentiation and/or metabolism. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of kinase-like protein, expression of kinase-like nucleic acid, or mutation content of kinase-like genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, an "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a kinase-like protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a kinase-like molecule or kinase-like modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a kinase-like molecule or kinase-like modulator of the invention, such as a modulator identified by one of the exemplary screening assays described herein.

The present invention further provides methods for identifying new agents, or combinations, that are based on identifying agents that modulate the activity of one or more of the gene products encoded by one or more of the kinase-like genes of the present invention, wherein these products may be associated with resistance of the cells to a therapeutic agent. Specifically, the activity of the proteins encoded by the kinase-like genes of the present invention can be used as a basis for identifying agents for overcoming agent resistance. By blocking the activity of one or more of the resistance proteins, target cells, will become sensitive to treatment with an agent that the unmodified target cells were resistant to.

Monitoring the influence of agents (e.g., drugs) on the expression or activity of a kinase-like protein can be applied in clinical trials. For example, the effectiveness of an agent determined by a screening assay as described herein to increase kinase-like gene expression, protein levels, or upregulate kinase-like activity, can be monitored in clinical trials of subjects exhibiting decreased kinase-like gene expression, protein levels, or downregulated kinase-like activity. Alternatively, the effectiveness of an agent determined by a screening assay to decrease kinase-like gene expression, protein levels, or downregulate kinase-like activity, can be monitored in clinical trials of subjects exhibiting increased kinase-like gene expression, protein levels, or upregulated kinase-like activity. In such clinical trials, the expression or activity of a kinase-like gene, and preferably, other genes that have been implicated in, for example, a kinase-like-associated disorder can be used as a "read out" or markers of the phenotype of a particular cell.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of kinase-like protein, expression of kinase-like nucleic acid, or mutation content of kinase-like genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a kinase-like modulator, such as a modulator identified by one of the exemplary screening assays described herein.

5. Monitoring of Effects During Clinical Trials

Monitoring the influence of agents (e.g., drugs, compounds) on the expression or activity of kinase-like genes (e.g., the ability to modulate aberrant cell proliferation and/or differentiation) can be applied not only in basic drug screening but also in clinical trials. For example, the effectiveness of an agent, as determined by a screening assay as described herein, to increase or decrease kinase-like gene expression, protein levels, or protein activity, can be monitored in clinical trials of subjects exhibiting decreased or increased kinase-like gene expression, protein levels, or protein activity. In such clinical trials, kinase-like expression or activity and preferably that of other genes that have been implicated in for example, a cellular proliferation disorder, can be assayed as a marker for the treatment using the treating agent.

For example, and not by way of limitation, genes that are modulated in cells by treatment with an agent (e.g., compound, drug, or small molecule) that modulates kinase-like activity (e.g., as identified in a screening assay described herein) can be identified. Thus, to study the effect of agents on cellular proliferation disorders, for example, in a clinical trial, cells can be isolated and RNA prepared and analyzed for the levels of expression of kinase-like genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of kinase-like genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of a kinase-like protein, mRNA, or genomic DNA in the preadministration sample; (3) obtaining one or more post-administration samples from the subject; (4) detecting the level of expression or activity of the kinase-like protein, mRNA, or genomic DNA in the postadministration samples; (5) comparing the level of expression or activity of the kinase-like protein, mRNA, or genomic DNA in the preadministration sample with the kinase-like protein, mRNA, or genomic DNA in the postadministration sample or samples; and (vi) altering the administration of the agent to the subject accordingly to bring about the desired effect, i.e., for example, an increase or a decrease in the expression or activity of a kinase-like protein.

C. Methods of Treatment

The present invention provides for both prophylactic and therapeutic methods of treating a subject at risk of (or susceptible to) a disorder or having a disorder associated with aberrant kinase-like expression or activity. Additionally, the compositions of the invention find use in the treatment of disorders described herein. Thus, therapies for disorders associated with CCC are encompassed herein.

1. Prophylactic Methods

In one aspect, the invention provides a method for preventing in a subject a disease or condition associated with an aberrant kinase-like expression or activity by administering to the subject an agent that modulates kinase-like expression or at least one kinase-like gene activity. Subjects at risk for a disease that is caused, or contributed to, by aberrant kinase-like expression or activity can be identified by, for example, any or a combination of diagnostic or prognostic assays as described herein. Administration of a prophylactic agent can occur prior to the manifestation of symptoms characteristic of the kinase-like aberrancy, such that a disease or disorder is prevented or, alternatively, delayed in its progression. Depending on the type of kinase-like aberrancy, for example, a kinase-like agonist or kinase-like antagonist agent can be used for treating the subject. The appropriate agent can be determined based on screening assays described herein.

2. Therapeutic Methods

Another aspect of the invention pertains to methods of modulating kinase-like expression or activity for therapeutic purposes. The modulatory method of the invention involves contacting a cell with an agent that modulates one or more of the activities of kinase-like protein activity associated with the cell. An agent that modulates kinase-like protein activity can be an agent as described herein, such as a nucleic acid or a protein, a naturally-occurring cognate ligand of a kinase-like protein, a peptide, a kinase-like peptidomimetic, or other small molecule. In one embodiment, the agent stimulates one or more of the biological activities of kinase-like protein. Examples of such stimulatory agents include active kinase-like protein and a nucleic acid molecule encoding a kinase-like protein that has been introduced into the cell. In another embodiment, the agent inhibits one or more of the biological activities of kinase-like protein. Examples of such inhibitory agents include antisense kinase-like nucleic acid molecules and anti-kinase-like antibodies.

These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a kinase-like protein or nucleic acid molecule. In one embodiment, the method involves administering an agent (e.g., an agent identified by a screening assay described herein), or a combination of agents, that modulates (e.g., upregulates or downregulates) kinase-like expression or activity. In another embodiment, the method involves administering a kinase-like protein or nucleic acid molecule as therapy to compensate for reduced or aberrant kinase-like expression or activity.

Stimulation of kinase-like activity is desirable in situations in which a kinase-like protein is abnormally down-regulated and/or in which increased kinase-like activity is likely to have a beneficial effect. Conversely, inhibition of kinase-like activity is desirable in situations in which kinase-like activity is abnormally upregulated and/or in which decreased kinase-like activity is likely to have a beneficial effect.

This invention is further illustrated by the following examples, which should not be construed as limiting.

EXPERIMENTAL

Example 1: 12832 Expression Analysis

Total RNA was prepared from various human tissues by single step extraction method using RNA STAT-60 according to the manufacturer's instructions (TelTest, Inc.). Each RNA preparation was treated with DnaseI (Ambion) at 37° C. for 1 hour. DNAse I treatment was determined to be complete if the sample required at least 38 PCR amplification cycles to reach a threshold level of fluorescence using β-2 microglobulin as an internal amplicon reference. The integrity of the RNA samples following DnaseI treatment was confirmed by agarose gel electrophoresis and ethidum bromide staining.

After phenol extraction, cDNA was prepared from the sample using the SuperScript™ Choice System following the manufacturers' instructions (GibcoBRL). A negative control of RNA without reverse transcriptase was mock reverse transcribed for each RNA sample.

Expression of the novel 12832 kinase-like gene sequence was measured by TaqMan® quantitative PCR (Perkine Elmer Applied Biosystems) in cDNA prepared from the following normal human tissues: prostrate, osteoclasts, liver, breast, skeletal muscle, brain, colon, heart, ovary, kidney, lung, vein, trachea, small intestine, thyroid, skin, testis, placenta, fetal liver, fetal heart, undifferentiated osteoblasts, differentiated osteoblasts, fetal spinal cord, spleen, thymus, tonsil, and lymph node.

Probes were designed by PrimerExpress software (PE Biosystems) based on the 12832 sequence. The primers and probes for expression analysis of 12832 and β-2 microglobulin were as follows:

```
12832 Forward Primer:
TTTTCACCTCCGACCTTTCCT                   (SEQ ID NO:3)

12832 Reverse Primer:
ATCCCTTCCATTGTGAAAGCC                   (SEQ ID NO:4)

12832 TaqMan Probe:
CCAGGCGGTGAGACTCTGGACTGAG               (SEQ ID NO:5)

β-2 microglobulin Forward Primer:
CACCCCCACTGAAAAATGA                     (SEQ ID NO:6)

β-2 microglobulin Reverse Primer:
CTTAACTATCTTGGGCTGTGACAAG               (SEQ ID NO:7)

β-2 microglobulin TaqMan Probe:
TATGCCTGCCGTGTGAACCACGTG                (SEQ ID NO:8)
```

The 12832 sequence probe was labeled using FAM (6-carboxyfluorescein), and the β-2 microglobulin reference was labeled with a different fluorescent dye, VIC. The differential labeling of the target kinase-like sequence and internal reference gene thus enabled measurement in the same well. Forward and reverse primers and probes for both the β-2 microglobulin and the targer 12832 sequence were added to the TaqMan Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target 12832 sequence. TaqMan matrix experiments were carried out on an ABI PRISM 7700 Sequence Detection System (PE Applied Biosystems). The thermal cycler conditions were as follows: hold for 2 min at 50 C and 10 min at 95 C, followed by two-step PCR for 40 cycles of 95° C. for 15 sec followed by 60° C. for 1 min.

The following method was used to quantitatively calculate 12832 expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the 12832 sequence is normalized by subtracting the Ct value of the β-2 microglobulin gene to obtain a $_\Delta Ct$ value using the following formula: $_\Delta Ct = Ct_{12832} - Ct_{\beta\text{-}2\ microglobulin}$. Expression is then calibrated against a cDNA sample showing a comparatively low level of expression of the 12832 sequence. The $_\Delta Ct$ value for the calibrator sample is then subtracted from $_\Delta Ct$ for each tissue sample according to the following formula: $_{\Delta\Delta} Ct = _\Delta Ct_{sample} - _\Delta Ct_{calibrator}$. Relative expression is then calculated using the arithmetic formula given by $2^{-\Delta\Delta Ct}$. Expression of the target 12832 sequence in each of the tissues tested was then graphically represented as discussed in more detail below.

FIG. 2 shows 12832 expression in synchronized WI-38 cells. WI-38 cells (human lung fibroblasts) were synchronized by serum starvation. RNA was harvested in 3 hour intervals for 24 hours to capture cells in various cell cycle phases. First strand cDNA was synthesized and Taqman was done using 12832 primers on time points 0, 3, 6, 9, 15, 18, 21, 24, and 27 hours. FIG. 2 shows the expression level of 12832 during each phase of the WI-38 cell cycle.

FIG. 3 shows 12832 expression versus cyclin B1 expression in synchronized WI-38 cells. Cyclin B1 is a marker for cell proliferation. The significant co-expression of cyclin B1 with 12832 supports the role of 12832 in tumor cell proliferation.

FIG. 4 shows 12821 expression in normal human lung tissue and in lung tumors. Taqman was done across a panel of human lung normal tissue and lung tumors. This Figure shows that 12832 expression is upregulated in 6/7 lung tumors verus normal lung tissue. The Y axis is relative expression. The X axis samples are as follows: PIT 241 normal lung, PIT 298 normal lung, MPI 131 normal lung, MPI 28 normal lung, CHT 813 lung (SSC), MPI 514 lung (tumor), CHT 752 lung (AC), CHT 799 lung (AC), CHT 800 lung (AC), CHT 817 lung (AC), MPI 150 lung (tumor). The numbers 2377 and 444 represent the true expression values of these two samples. (AC represents adenocarcinoma; SSC represents squamous cell carcinoma).

FIG. 5 shows 12832 expression versus cyclin B1 expression in lung. Taqman across a panel of normal lung tissue and lung tumors shows 12832 expression correlates with cyclin B1 expression indicating a potential role in lung tumor cell proliferation. (AC represents adenocarcinoma; SCC represents squamous cell carcinoma).

FIG. 6 shows 12832 gene expression in normal human tissues. Taqman across a panel of normal human tissue shows 12832 expression in proliferative normal tissues such as the testis and fetal liver and heart. (Y axis represents relative expression values).

Figure 7:
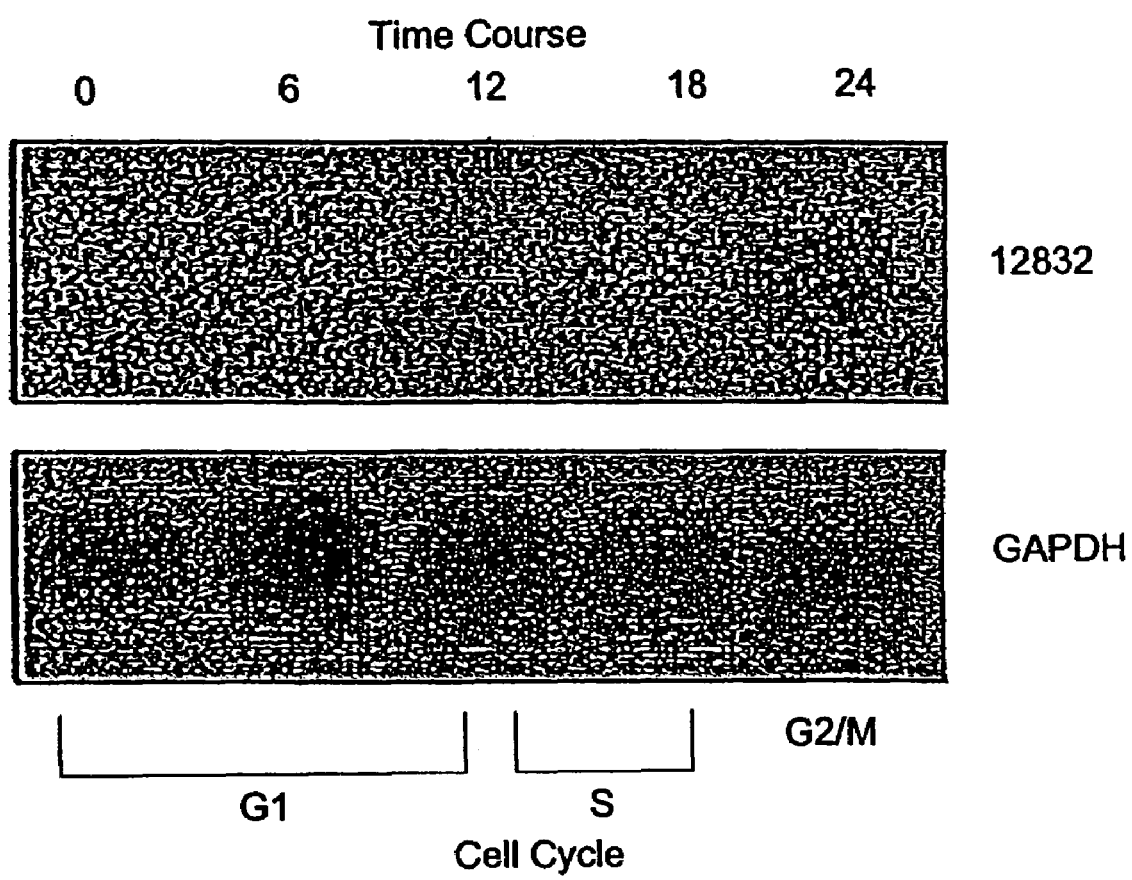
FIG. 7 shows 12832 expression during a cell cycling event in a Northern Blot experiment wherein the expression of 12832 is upregulated as the cells transition from the S phase into the $G_2/M$ phase of the cell cycle.

FIG. 7 shows 12832 expression during a cell cycling event in a Northern Blot experiment wherein the expression of 12832 is upregulated as the cells transition from the S phase into the $G_2/M$ phase of the cell cycle.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated antibody or antibody fragment which selectively binds polypeptide selected from the group consisting of:
   a) SEQ ID NO: 2; and
   b) a fragment of the 12832 amino acid sequence of SEQ ID NO: 2, wherein the fragment has a 12832 kinase protein activity and comprises at least 7-5 50 contiguous amino acids of SEQ ID NO: 2.

2. The antibody or antibody fragment of claim 1, wherein the antibody or antibody fragment is a monoclonal antibody or a monoclonal antibody fragment.

3. The antibody or antibody fragment of claim 1, wherein the antibody or antibody fragment is a chimeric, humanized, or human antibody or a chimeric, humanized, or human antibody fragment.

4. The monoclonal antibody or monoclonal antibody fragment of claim 2, wherein the monoclonal antibody or monoclonal antibody fragment is conjugated to a therapeutic moiety.

5. The antibody or antibody fragment of claim 4 wherein the therapeutic moiety is a cytotoxin, a therapeutic agent or a radioactive metal ion.

6. The monoclonal antibody or monoclonal antibody fragment of claim 2, wherein the monoclonal antibody or monoclonal antibody fragment is coupled to a detectable label.

7. A kit comprising the antibody or antibody fragment of claim 1, and instructions for use.

8. The antibody or antibody fragment of claim 1, wherein the antibody or antibody fragment selectively binds a fragment of the 12832 amino acid sequence of SEQ ID NO:2, wherein the fragment has a 12832 kinase protein activity, comprises at least 50 contiguous amino acids of SEQ ID NO:2 and further comprises the active site signature at amino acids 163 to 175 of SEQ ID NO:2.

9. The antibody or antibody fragment of claim 1, wherein the antibody or antibody fragment selectively binds a fragment of the 12832 amino acid sequence of SEQ ID NO:2, wherein the fragment has a 12832 kinase protein activity and comprises the kinase domain at amino acids 32 to 316 of SEQ ID NO:2.

10. An antibody or antibody fragment which selectively binds to an isolated polypeptide consisting of the amino acid sequence of SEQ ID NO:2.

11. The antibody or antibody fragment of claim 10, wherein the antibody or fragment is coupled to a detectable label.

12. A kit comprising the antibody or antibody fragment of claim 10, and instructions for use.

13. A method for detecting the presence of a polypeptide comprising SEQ ID NO: 2 in a sample, comprising:
   a) contacting the sample with the antibody or antibody fragment of claim 1; and
   b) determining whether the compound binds to the polypeptide in the sample.

14. The method of claim 13, wherein the antibody or antibody fragment is coupled to a detectable label.

* * * * *